US009546962B2

(12) United States Patent
Sullivan et al.

(10) Patent No.: US 9,546,962 B2
(45) Date of Patent: Jan. 17, 2017

(54) MULTI-SPOT SCANNING COLLECTION OPTICS

(71) Applicant: KLA-Tencor Corporation, Milpitas, CA (US)

(72) Inventors: Jamie M. Sullivan, Eugene, OR (US); Ralph Johnson, Los Gatos, CA (US); Evegeny Churin, San Jose, CA (US); Wenjian Cai, Sunnyvale, CA (US); Yong Mo Moon, San Ramon, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/619,004

(22) Filed: Feb. 10, 2015

(65) Prior Publication Data
US 2015/0226677 A1 Aug. 13, 2015

Related U.S. Application Data

(60) Provisional application No. 61/939,140, filed on Feb. 12, 2014.

(51) Int. Cl.
*G01N 21/00* (2006.01)
*G01N 21/88* (2006.01)
(Continued)

(52) U.S. Cl.
CPC ...... *G01N 21/8806* (2013.01); *G01N 21/8851* (2013.01); *G01N 21/9501* (2013.01);
(Continued)

(58) Field of Classification Search
CPC ............ G01N 21/8851; G01N 21/8806; G01N 21/956; G01N 2201/06113; G01N 2201/106; G01N 2201/1056; G02B 27/4227
(Continued)

(56) References Cited

U.S. PATENT DOCUMENTS 3,977,772 A 8/1976 Rimmer et al.
5,602,400 A * 2/1997 Kawashima .......... G03F 9/7026
250/548
(Continued)

FOREIGN PATENT DOCUMENTS

JP H09196859 A 7/1997

OTHER PUBLICATIONS

"Int'l Application Serial No. PCT/US2015/015704, Search Report mailed May 18, 2015", 3 pgs.

*Primary Examiner* — Hoa Pham
(74) *Attorney, Agent, or Firm* — Kwan & Olynick LLP

(57) ABSTRACT

Disclosed are apparatus and methods for inspecting or measuring a specimen. A system comprises an illumination channel for generating and deflecting a plurality of incident beams to form a plurality of spots that scan across a segmented line comprised of a plurality of scan portions of the specimen. The system also includes one or more detection channels for sensing light emanating from a specimen in response to the incident beams directed towards such specimen and collecting a detected image for each scan portion as each incident beam's spot is scanned over its scan portion. The one or more detection channels include at least one longitudinal side channel for longitudinally collecting a detected image for each scan portion as each incident beam's spot is scanned over its scan portion.

20 Claims, 26 Drawing Sheets

(51) Int. Cl.
  *G02B 27/42* (2006.01)
  *G01N 21/95* (2006.01)
  *G02B 21/00* (2006.01)
  *G02B 27/46* (2006.01)
(52) U.S. Cl.
  CPC ....... *G02B 21/002* (2013.01); *G02B 21/0016* (2013.01); *G02B 21/0092* (2013.01); *G02B 27/4227* (2013.01); *G02B 27/46* (2013.01); *G01N 2201/06113* (2013.01); *G01N 2201/1056* (2013.01)
(58) Field of Classification Search
  USPC ........................................... 356/237.1–237.5
  See application file for complete search history.

(56) References Cited

U.S. PATENT DOCUMENTS

| | | | |
|---|---|---|---|
| 6,043,932 A | 3/2000 | Kusunose | |
| 6,208,411 B1 * | 3/2001 | Vaez-Iravani | G01N 21/956 356/237.2 |
| 6,236,454 B1 | 5/2001 | Almogy | |
| 6,578,961 B2 | 6/2003 | Vaez-Iravani | |
| 6,636,301 B1 | 10/2003 | Kvamme et al. | |
| 6,775,051 B2 * | 8/2004 | Sullivan | G02B 26/10 359/286 |
| 6,879,390 B1 * | 4/2005 | Kvamme | G01N 21/8806 356/237.2 |
| 6,922,236 B2 | 7/2005 | Vaez-Iravani et al. | |
| 7,030,978 B2 | 4/2006 | Guetta et al. | |
| 7,053,395 B2 | 5/2006 | Feldman et al. | |
| 7,130,036 B1 | 10/2006 | Kuhlmann et al. | |
| 7,397,557 B2 | 7/2008 | Jeong et al. | |
| 7,463,349 B1 | 12/2008 | Biellak et al. | |
| 7,489,393 B2 | 2/2009 | Biellak et al. | |
| 7,492,451 B2 | 2/2009 | Vaez-Iravani et al. | |
| 8,402,785 B2 | 3/2013 | Chen et al. | |
| 8,891,079 B2 | 11/2014 | Zhao et al. | |
| 8,995,746 B2 * | 3/2015 | Cao | G06T 7/0004 382/145 |
| 9,395,340 B2 * | 7/2016 | Sullivan | G01N 29/2418 |
| 2003/0011760 A1 * | 1/2003 | Vaez-Iravani | G01N 21/47 356/237.2 |
| 2003/0179370 A1 | 9/2003 | Goldberg et al. | |
| 2006/0056028 A1 | 3/2006 | Wildnauer | |
| 2009/0103078 A1 * | 4/2009 | Ishimaru | G01N 21/474 356/237.2 |
| 2009/0161096 A1 | 6/2009 | Vaez-Iravani et al. | |
| 2009/0225399 A1 | 9/2009 | Zhao et al. | |
| 2010/0165340 A1 | 7/2010 | Xu et al. | |
| 2013/0114085 A1 | 5/2013 | Wang et al. | |
| 2013/0250582 A1 | 9/2013 | Zhao et al. | |
| 2014/0016125 A1 | 1/2014 | Sullivan et al. | |
| 2014/0260640 A1 | 9/2014 | Sullivan et al. | |
| 2015/0370175 A1 * | 12/2015 | Nicolaides | G03F 7/7085 355/77 |

* cited by examiner

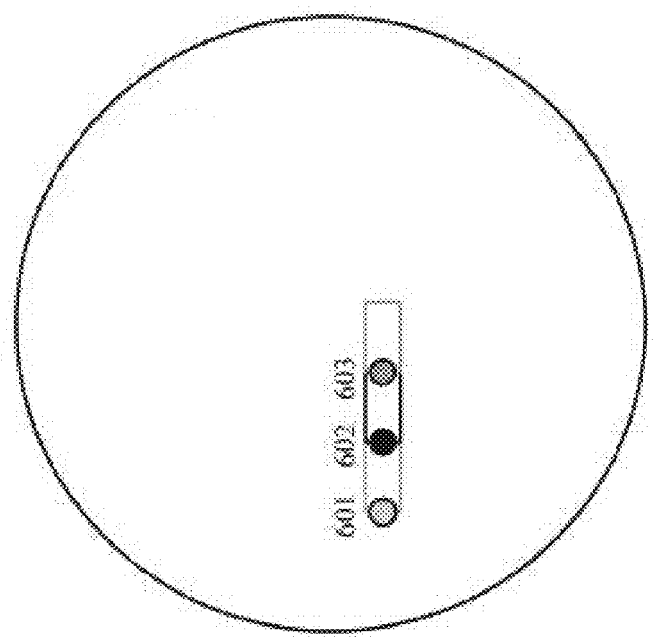
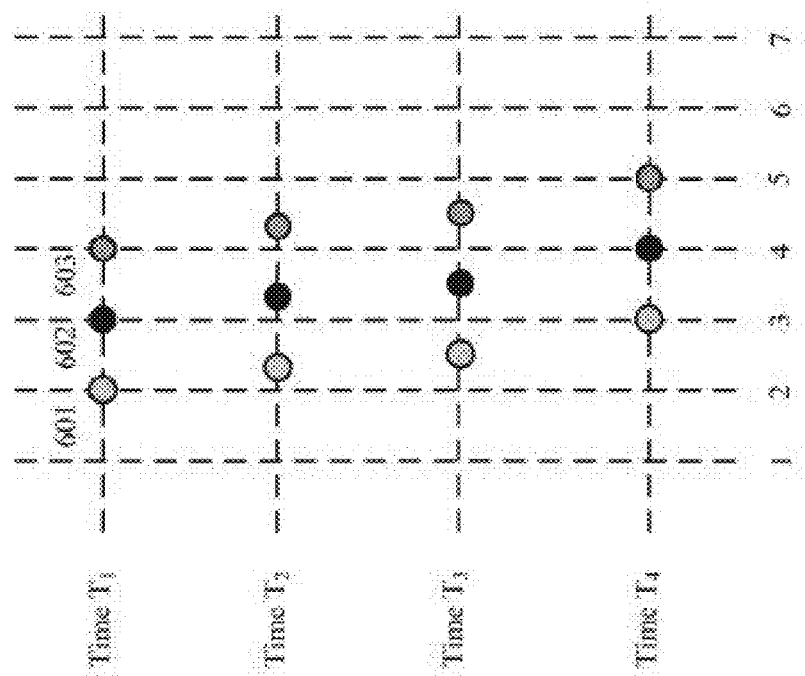
Figure 6B
Figure 6A

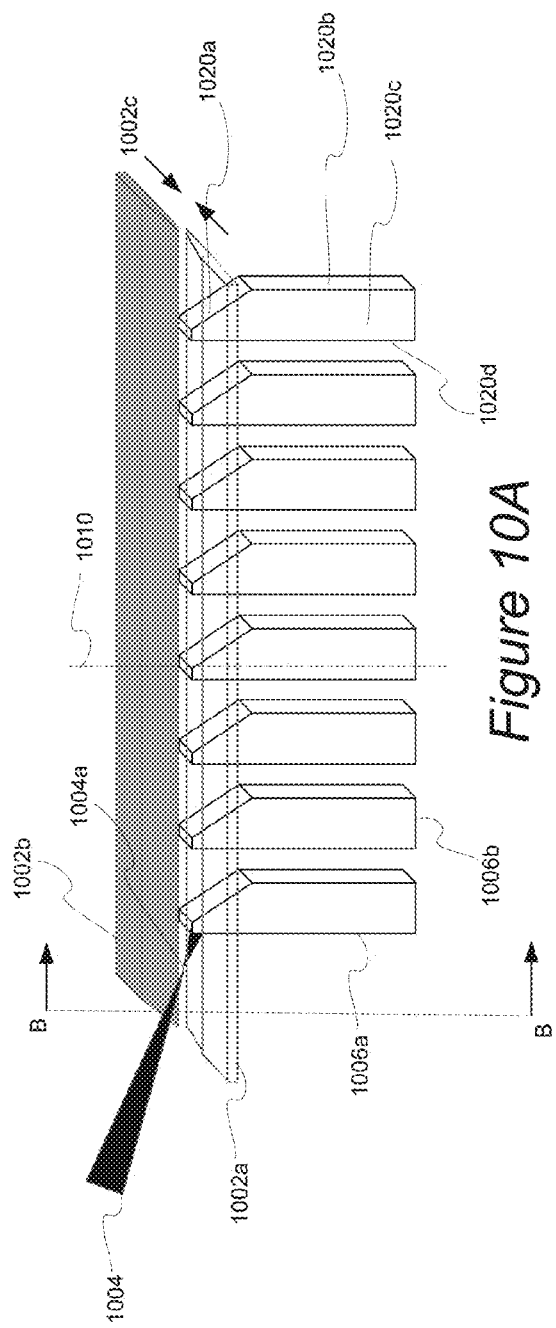
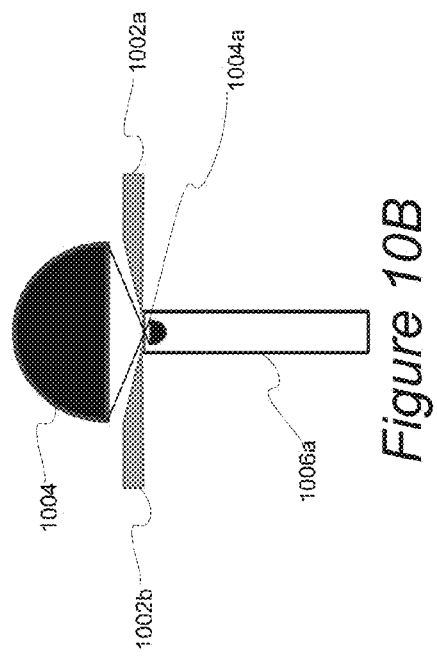

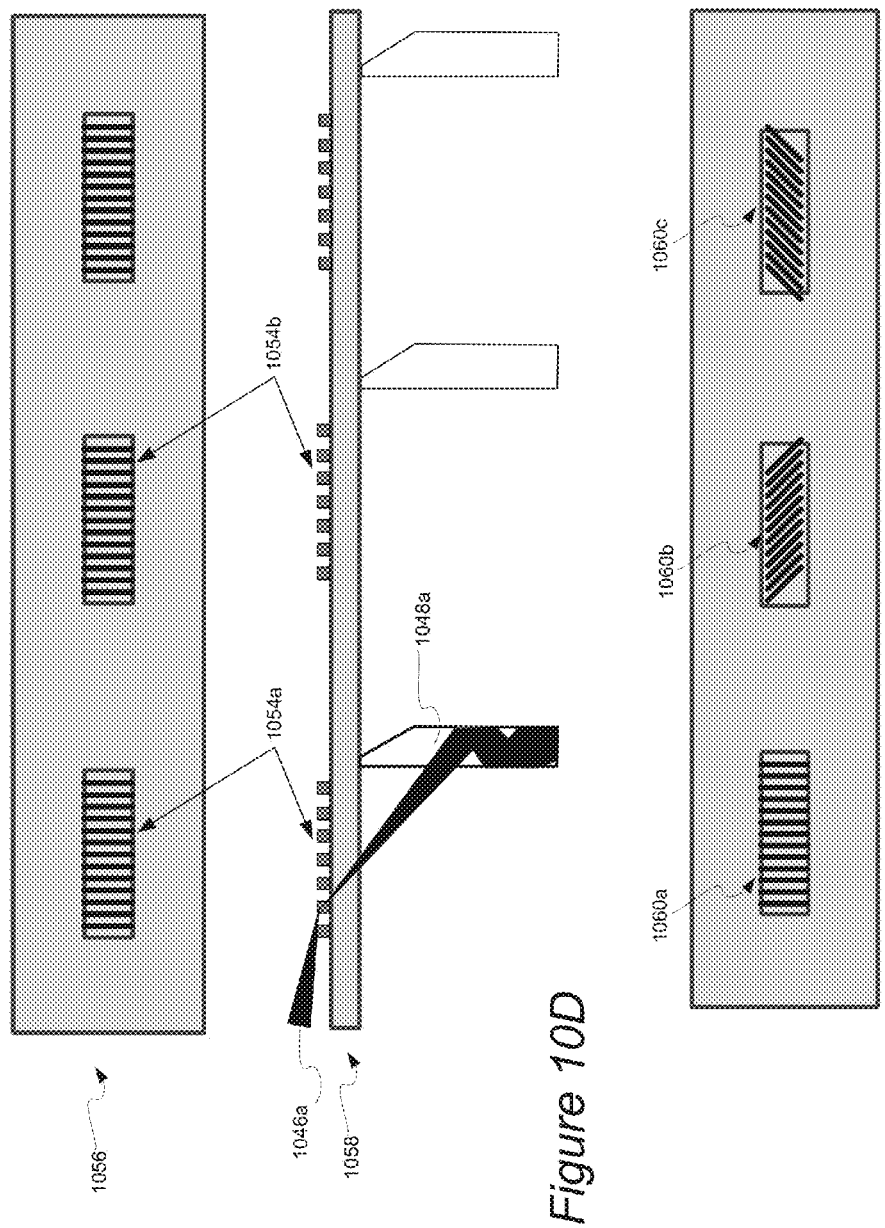

MULTI-SPOT SCANNING COLLECTION OPTICS

CROSS-REFERENCE TO RELATED APPLICATIONS

This application claims priority of U.S. Provisional Patent Application No. 61/939,140, entitled Multi-Spot Scanning Collection Optics, filed 12 Feb. 2014 by Jamie Sullivan et al., which application is incorporated herein by reference in its entirety for all purposes.

TECHNICAL FIELD OF THE INVENTION

The present invention relates generally to inspection and metrology systems. More specifically, it relates to scanning type systems for inspecting and measuring semiconductor wafers and other types of patterned samples.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. Each device needs to be fault free prior to shipment to the end users or customers.

Various inspection and metrology systems are used within the semiconductor industry to detect defects on a semiconductor reticle or wafer. Some conventional optical inspection tools locate defects on patterned wafers by scanning the surface of the wafer with a tightly focused laser spot and measuring the amount of light scattered by the illuminated spot on the wafer. Dissimilarities in the scattering intensity between similar locations in adjacent dies are recorded as potential defect sites. Other types of metrology systems are used to measure various characteristics, such as critical dimension (CD) on a reticle or wafer.

There is a continuing need for improved inspection and metrology systems, including scanning type systems.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

Disclosed is a system for inspecting or measuring a specimen. The system includes an illumination channel for generating and scanning a plurality of incident beams to form a plurality of spots that scan across a segmented line comprised of a plurality of scan portions of the specimen. The system further includes one or more detection channels for sensing light emanating from a specimen in response to the incident beams directed towards such specimen and collecting a detected image for each scan portion as each incident beam's spot is scanned over its scan portion. The one or more detection channels include at least one longitudinal side channel for longitudinally collecting a detected image for each scan portion as each incident beam's spot is scanned over its scan portion.

In a specific implementation, the detection channels include a first longitudinal side channel for longitudinally collecting a first plurality of detected images for the scan portions, a second longitudinal side channel for longitudinally collecting a second plurality of detected images for the scan portions, and a normal channel for collecting a third plurality of detected images for the scan portions. The first longitudinal side channel is positioned opposite of the second longitudinal side channel. In a further aspect, the illumination channel includes a normal illumination sub-channel for generating and scanning a first set of the plurality of incident beams to contribute to the plurality of spots that scan across the plurality of scan portions of the specimen and an oblique illumination sub-channel for generating and scanning a second set of the plurality of incident beams to contribute to the plurality of spots that scan across the plurality of scan portions of the specimen.

In a further aspect, the first longitudinal side channel comprises a first front lens arranged for receiving the first output beams that are scattered from the scan portions and directing such first output beams through a Fourier plane towards a first back lens arranged for receiving and directing the first output beams towards a first sensor module arranged for separately sensing the first output beams from the first back lens. The second longitudinal side channel includes similar components. The normal channel includes output optics for collecting and directing the third set of output beams towards a third sensor module arranged for separately sensing the third output beams. In yet a further aspect, the first longitudinal side channel further includes a first optics element arranged for receiving the first output beams from the first front lens, spatially filtering portions of the first output beams at the Fourier plane, and directing the first output beams to the first back lens. The second and third optics elements include similar components.

In yet another embodiment, the first, second, and third optics element each include an aperture having serrated teeth pointed perpendicular to an optical axis for controlling diffraction. In a further aspect, the serrated teeth of each of the first and second, and third optics elements are formed from two overlaid masks with serrated teeth so as to cover rounded portions of the serrated teeth in each mask and to form non-rounded serrated teeth. In one example, the first, second, and third optics element each include a plurality of pins that are independently movable to drop down into each aperture and selectively block noise, isolate signals, or block one or more diffraction spots.

In yet another embodiment, the normal and oblique illumination sub-channels each includes a magnifier changer. In a further aspect, the normal, first and second longitudinal side channels exclude a magnifier changer so as to have a fixed magnification for the first, second, and third output beams. The normal and oblique illumination sub-channels each include a diffractive optical element (DOE) positioned after such sub-channel's magnifier changer, and the DOE's of the normal and oblique illumination sub-channels generate the first and second set of incident beams, respectively, so that the first and second set of incident beams have a same center scan position at different magnifications. The first, second, and third sensor modules include a first, second, and third spot separator mechanism, respectively, that are sized and positioned to separately receive the first, second, third output beams, respectively, at a highest and lowest magnification without movement of such spot separator mechanism. In a further example, the normal and oblique illumination sub-channels each include a scan mechanism that is configured to sweep the first and second set of output beams across equally sized scan portions on the sample. In another embodiment, the normal channel and the first and second longitudinal side channels each include a magnifier changer to match a magnification of the magnifier changer of the normal and oblique illumination sub-channels.

In another implementation, the first sensor module includes a first and second razor portion forming a first gap there between arranged to receive a focus point for each of the first output beams and a first plurality of prisms that are each positioned at each of the first output beams' focus point so as to separately receive and direct the first output beams to a plurality of first fiber elements arranged to separately receive and direct the first output beams to a first plurality of focusing elements for individually focusing the first output beams onto a plurality of first sensor elements for individually sensing the first output beams. The second and third sensor modules have similar components. In a further aspect, the first, second, and third prisms are movable to compensate for distortion.

In another embodiment, the first sensor module includes a first plurality of mirror and/or fiber elements sets that are each positioned at each of the first output beams' focus point so as to separately receive and direct the first output beams to the first plurality of focusing elements, and the second and third sensor modules have similar mirrors. In another example, the first sensor module includes a mask having a plurality of apertures that each receive a focus point for each of the first output beams and prisms or sets of mirrors that are each positioned at each of the first output beams' focus point so as to separately receive and direct the first output beams to a plurality of first fiber elements. The second and third sensor modules include similar components. In a further aspect, each of the first, second, and third masks includes a grating in each aperture directing the first, second, and third output beams, respectively towards the first, second, and third sensor elements, respectively. In another aspect, at least some of the gratings of the first, second, and third mask have orientations in different directions. In yet another example, the gratings of the first, second, and third mask have orientations in a same direction.

In an alternative embodiment, the invention pertains to a method of inspecting a specimen, and the method includes (i) scanning multiple incident beams over separated scan lines of the specimen, (ii) receiving and separating output beams scattered from the separated scan lines of the specimen in response to the incident beams, (iii) longitudinally directing each separated output beam towards a sensor to longitudinally generate an image or signal, and (iv) detecting defects or measuring a characteristic of the specimen based on the image or signal from each sensor.

These and other aspects of the invention are described further below with reference to the figures.

BRIEF DESCRIPTION OF THE DRAWINGS

FIGS. 6A and 6B illustrate exemplary sweeps of three small spots.

FIG. 10A is a diagrammatic side view of a spot isolator using prisms and slits for the collection system used to capture light scattered from multiple scanning beams in accordance with a specific implementation of the present invention.

FIG. 10B is a diagrammatic representation of the spot separator and prisms as viewed in direction B-B of FIG. 10A.

FIG. 10D is a diagrammatic representation of a mask type spot separator with gratings in accordance with an alternative embodiment of the present invention.

FIG. 10E illustrates a top view of a mask type spot isolator with gratings that are oriented in different directions in accordance with another embodiment of the present invention.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Introduction

Figure 1:
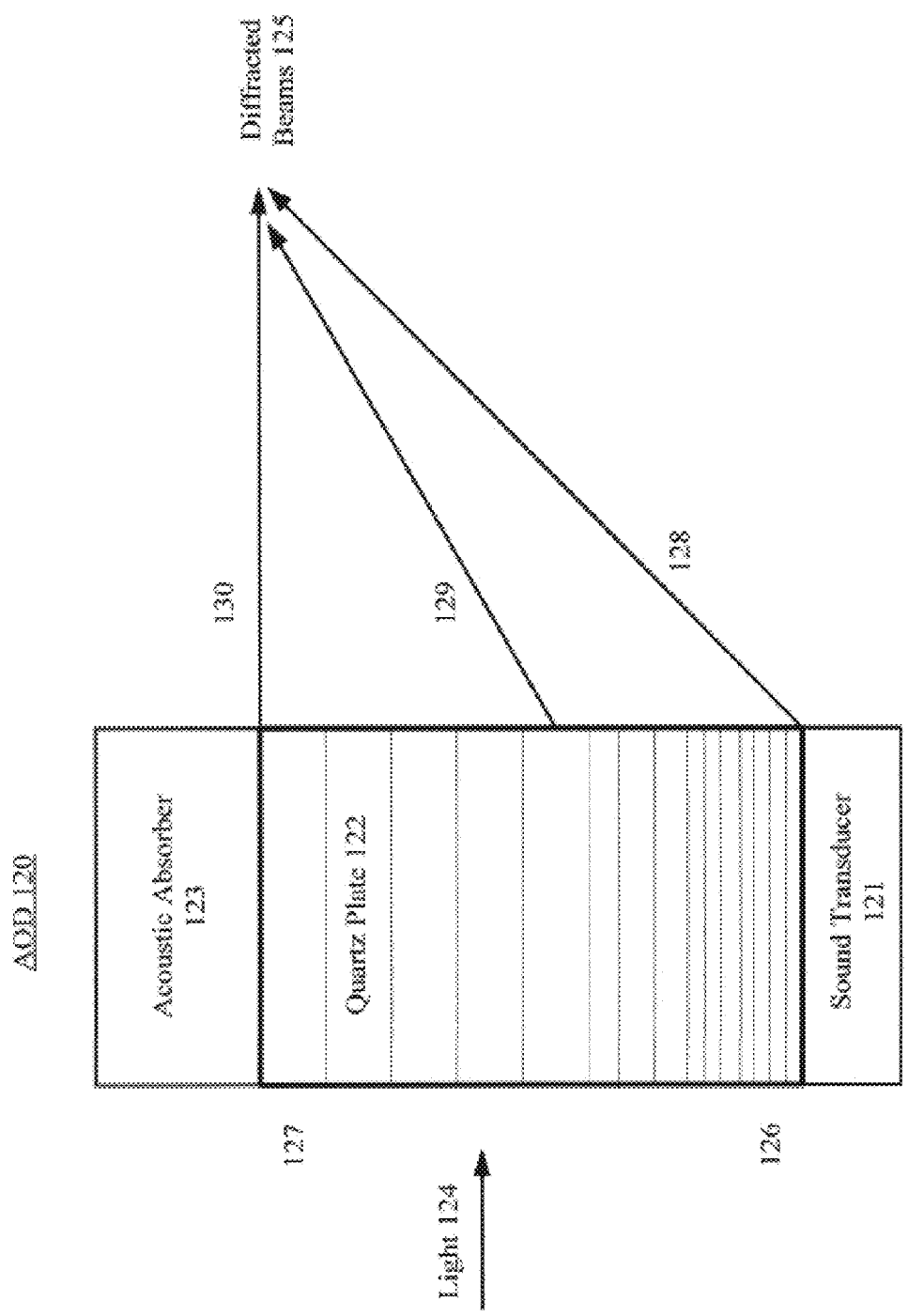
FIG. 1 illustrates a simplified configuration of an acousto-optical device (AOD).

Some scanning systems include an illumination system having one or more incident beam sources for scanning or sweeping one or more beams across the wafer. The scanning system may specifically include an acousto-optic deflector (AOD) and a mechanism for controlling the AOD's deflection characteristics. For instance, a clock may be used to generate a "chirp" signal input to each AOD. For example, FIG. 1 illustrates a simplified configuration of an acousto-optical device (AOD) 120. AOD 120 includes a sound transducer 121, an acousto optic medium such as quartz 122, and an acoustic absorber 123. Other acousto optic medium materials, besides quartz, can be utilized, depending on the particular wavelength requirements of the system. The acoustic absorber could be a cut in the acousto optic medium 122. An oscillating electric signal can drive sound transducer 121 and cause it to vibrate. In turn, this vibration creates sound waves in quartz plate 122. Acoustic absorber 123 can be formed from a material that absorbs any sound waves that reach the edge of quartz plate 122. As a result of the sound waves, incoming light 124 to quartz plate 122 is diffracted into a plurality of directions 128, 129 and 130.

A diffracted beam emerges from quartz plate 122 at an angle that depends on the wavelength of the light relative to the wavelength of the sound. By ramping frequencies from low to high, portion 126 may have a higher frequency than portion 127. Because portion 126 has a higher frequency, it diffracts a portion of the incident light beam through a steeper angle as shown by diffracted beam 128. Because portion 127 has a relatively lower frequency, it diffracts a portion of the incident light beam through a more shallow angle as shown by diffracted light beam 130. Because a mid-section portion between portions 126 and 127 has a frequency between the higher and relatively lower frequencies, it diffracts a portion of the incident light beam through an intermediate angle as shown by diffracted light beam 129. Thus, an AOD can be used to focus an incoming beam 124 at position 125.

Figure 2A:
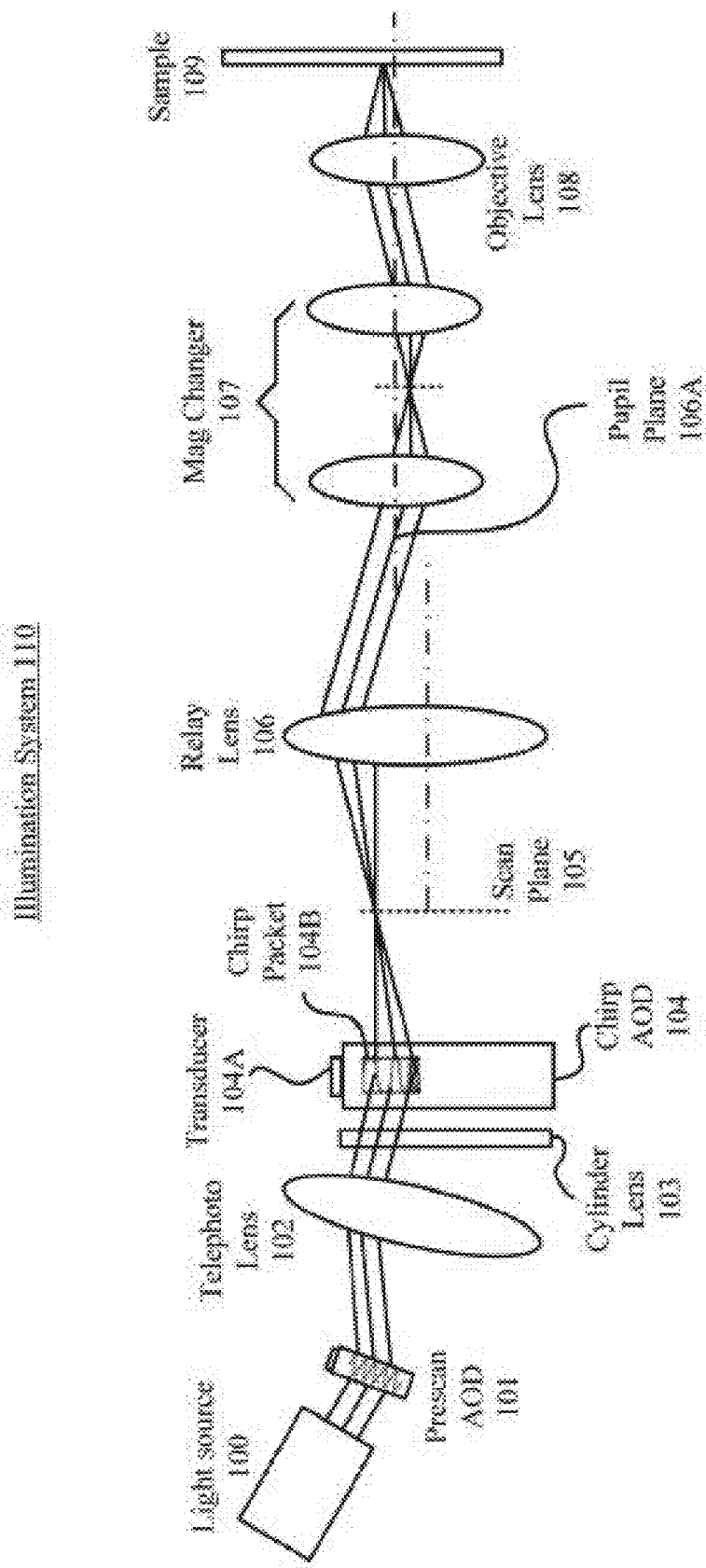
FIG. 2A illustrates an exemplary dual AOD illumination system configured to generate and scan a beam across a sample, such as a wafer.

FIG. 2A illustrates an exemplary dual AOD illumination system 110 configured to generate and scan a beam across a sample 109, such as a wafer. A prescan AOD 101 can be used to deflect the incident light from a light source 100 at an angle, wherein the angle is proportional to the frequency of the radio frequency (RF) drive source. A telephoto lens 102 can be used to convert the angular scan from prescan AOD 101 into a linear scan.

Figure 2B:
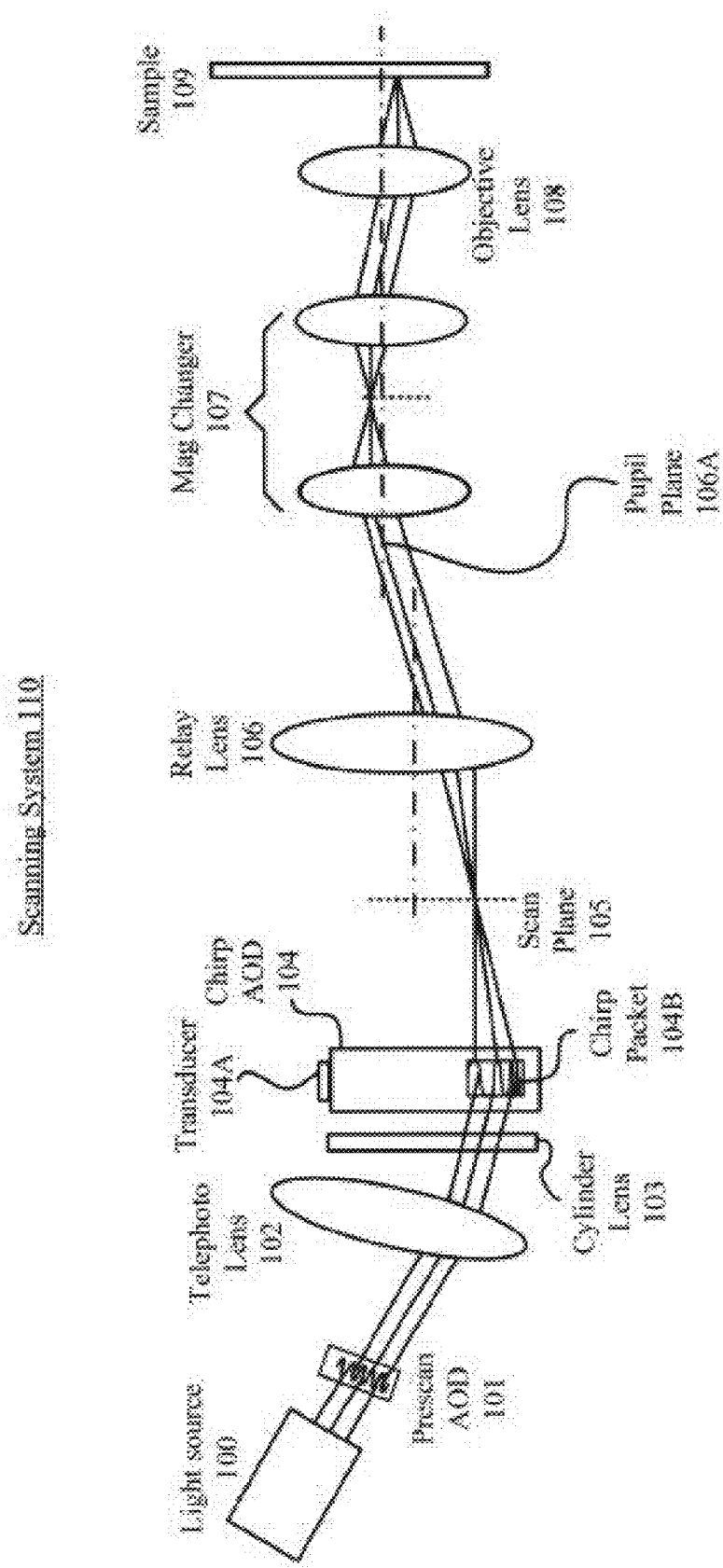
FIG. 2B illustrates the location of a chirp packet at the end of a spot sweep of the dual AOD illumination system shown in FIG. 2A.

A chirp AOD 104 can be used to focus the incident beam in the plane of acoustic propagation onto a scan plane 105, which can be accomplished by ramping thru all the RF frequencies with transducer 104A faster than those frequencies can all propagate thru chirp AOD 104. This rapid ramping forms a chirp packet 104B. Chirp packet 104B then propagates thru chirp AOD 104 at the speed of sound. FIG. 2A shows the location of chirp packet 104B at the start of a spot sweep, whereas FIG. 2B illustrates the location of chirp packet 104B at the end of that spot sweep. Note that during this propagation, prescan AOD 101 can adjust its RF frequency to track the chirp packet in AOD 104 to keep the light beam incident upon chirp packet 104B.

A cylinder lens 103 can be used to focus the beam in a plane perpendicular to the plane of acoustic propagation. A relay lens 106 can be used to generate a real pupil at a pupil plane 106A. A magnification changer 107 can be used to adjust the size of the spot and the length of sweep. An objective lens 108 can then be used to focus the spot onto a sample 109, such as a wafer.

Other systems may utilize a beam expander in place of the pre-scan AOD to form a "flood AOD" system. In a flood AOD configuration (not shown), a single or multiple chirp packets (not shown) can be generated in AOD 104. Since the entire AOD is flooded with light from the beam expander, AOD 104 focuses the light incident on each chirp packet and, thus, each chirp packet generates its own spot. Therefore objective lens 108 focuses one or more spots onto sample 109 simultaneously (not shown).

When an AOD that produces multiple chirp packets is used to generate multiple spots, a larger AOD is needed since each chirp packet has a finite size as a result of the time required to ramp through the required RF frequencies. The more chirp packets; the larger the AOD required. Additionally, each of the chirp packets is attenuated as it travels along the length of the AOD. Thus, a larger AOD results in larger attenuation losses than a smaller AOD. Conversely, an AOD that has closer multiple chirp packets and, thus, scanning spots in close proximity to one another results in more crosstalk between scanning spots Note that sample 109 is typically placed on an XY translation stage capable of bi-directional movement. In this configuration, the stage can be moved so that the focused spots (formed by the focusing optics using the diffracted light beams) impinging sample 109 can be scanned along adjacent contiguous strips of equal width (e.g., raster scan lines). U.S. Pat. No. 4,912,487, issued to Porter et al. on Mar. 27, 1990, and incorporated by reference herein, describes exemplary illumination systems including a translation stage configured to provide raster scanning.

Example Illumination Embodiments

Figure 3A:
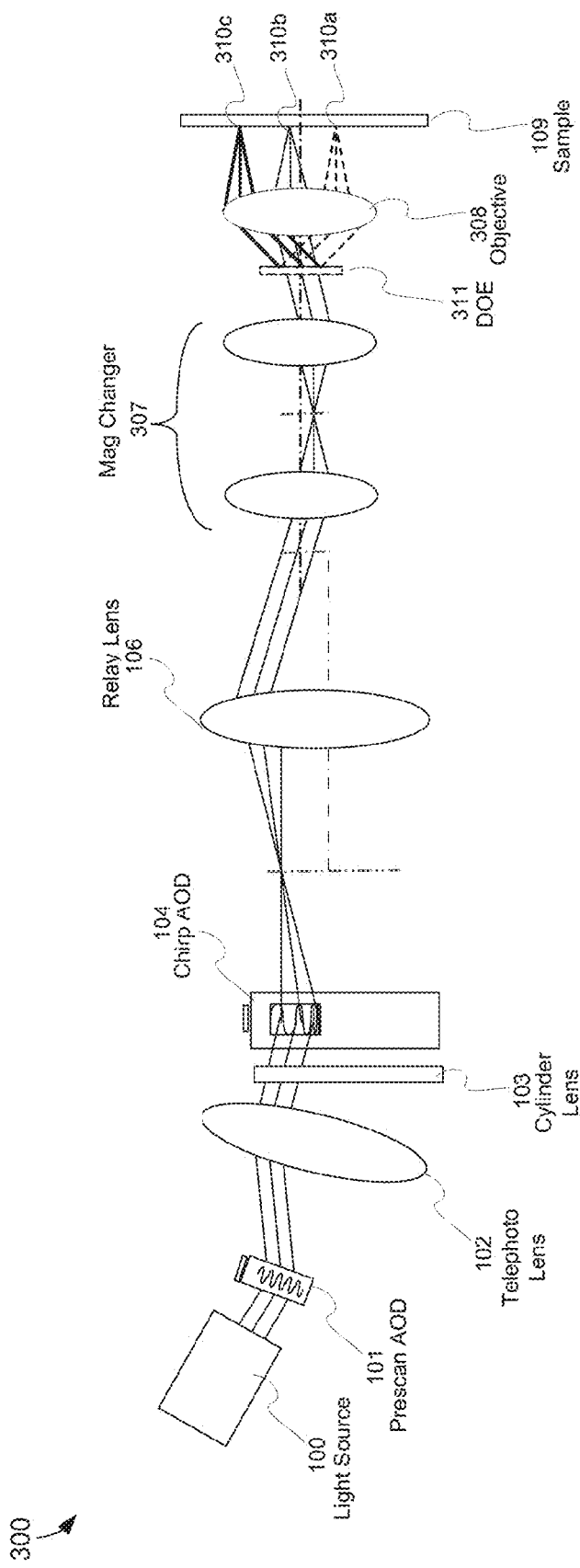
FIG. 3A illustrates a diagrammatic AOD illumination system that generates multiple scanning spots with variable magnification, which can be imaged using a fixed collection magnification, in accordance with one embodiment of the present invention.

FIG. 3A illustrates a diagrammatic AOD illumination system 300 that generates multiple scanning spots with variable magnification, which can be imaged using a fixed collection magnification, in accordance with one embodiment of the present invention. In this embodiment, a diffractive optical element (DOE) 311 can be positioned after magnifier changer 307 to generate a plurality of spots. Although FIG. 3A shows three spots being generated, other embodiments can generate a different number of spots.

Figure 3B:
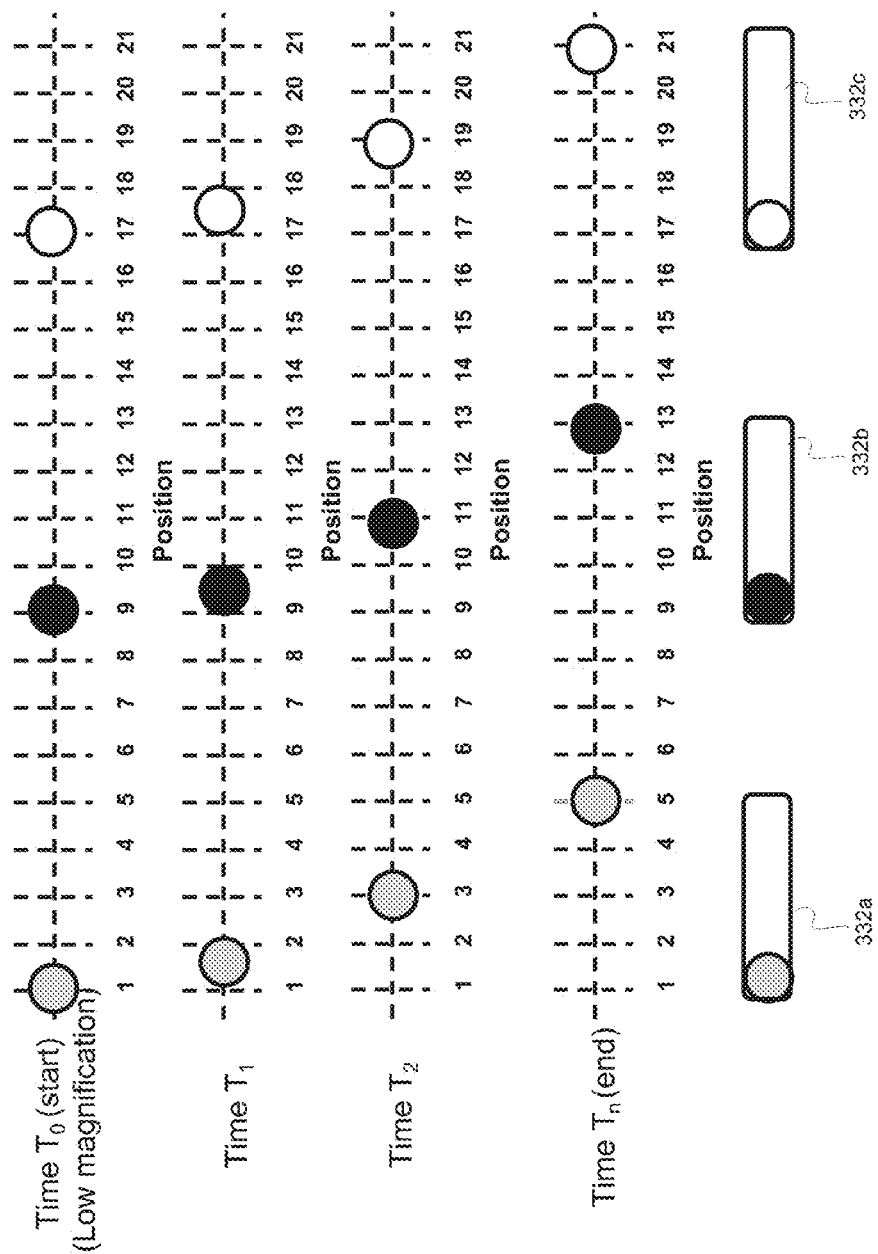
FIG. 3B illustrates the sweep positions for three spots under a low magnification in accordance with a first implementation.
Figure 3C:
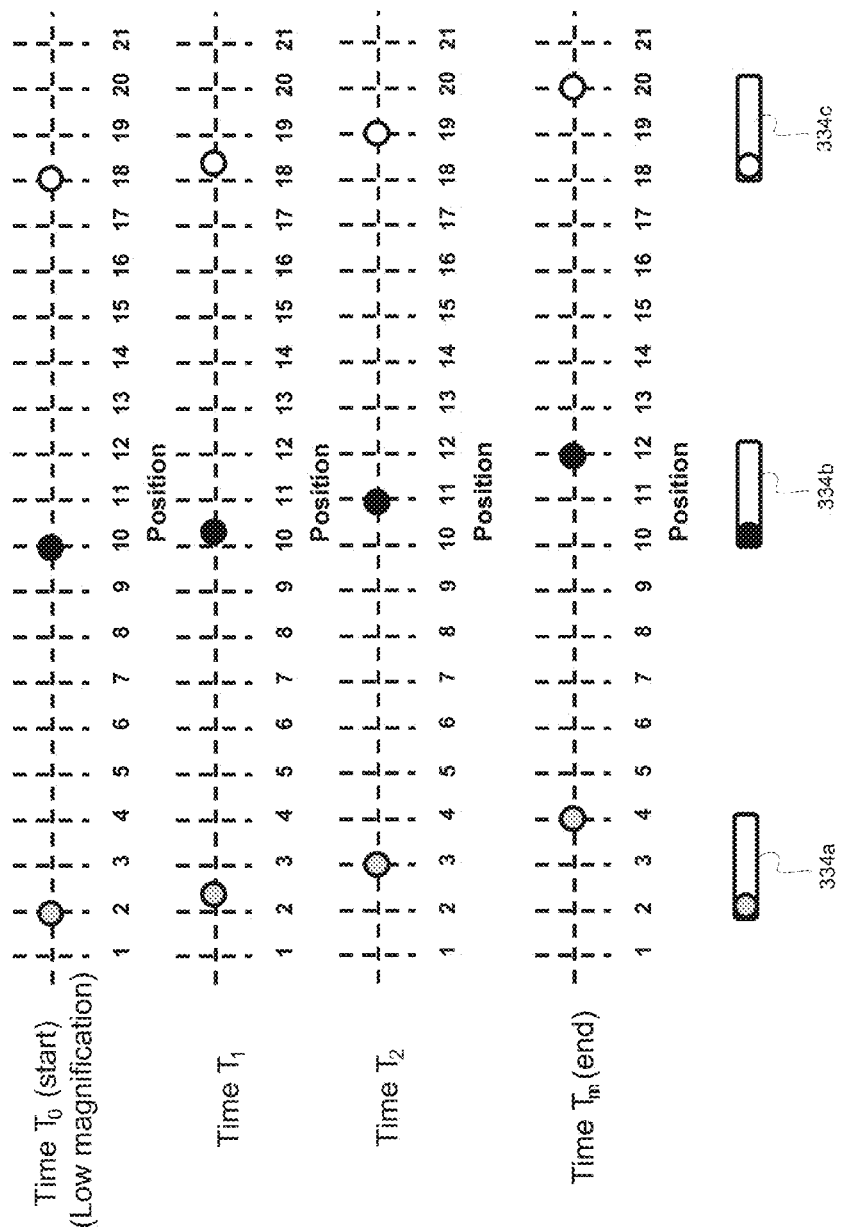
FIG. 3C illustrates the sweep positions for three spots under a high magnification in accordance with a first implementation.
Figure 3D:
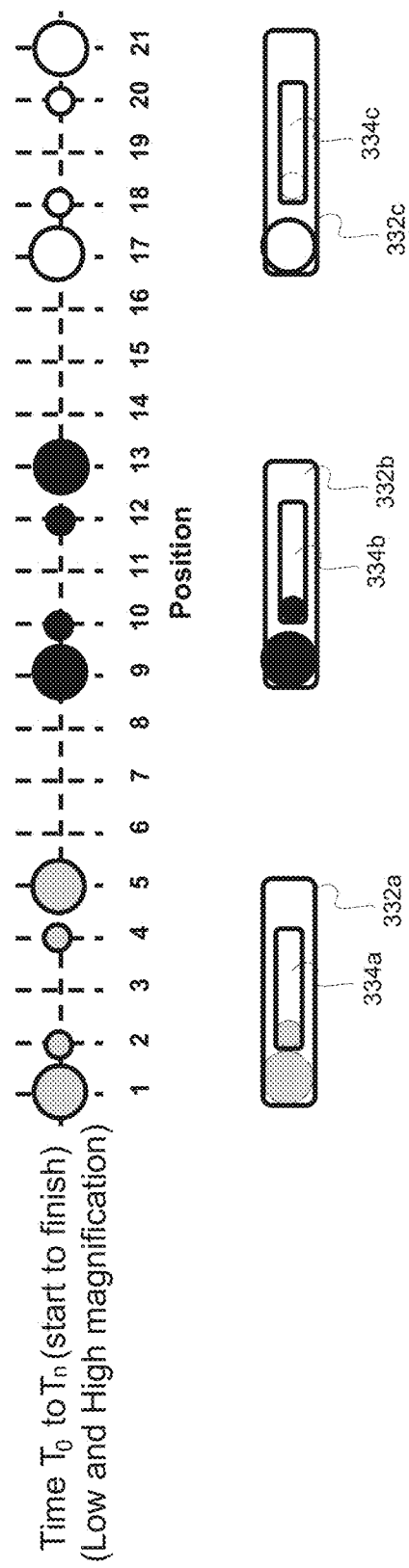
FIG. 3D illustrates the relative sweep positions for both low and high magnification in accordance with a first implementation.

In the illustrated example, DOE 311 generates the three spots after the illumination beam has been magnified by magnifier changer 307. That is, DOE 311 causes three beams (shown by dark lines, light lines, and dashed lines) to form three spots 310a, 310b, 310c on sample 109. FIG. 3B~3D illustrate the effects of changing the magnification of magnifier changer 307 on the spot size, spot spacing, and scan length on sample 109 for illumination system 300. The three different spots are illustrated with different gray levels (gray, black, and white), which correspond to the three spot positions 310a, 310b, and 310c, respectively, of FIG. 3A.

FIG. 3B illustrates the sweep positions for three spots under a low magnification in accordance with one embodiment. For example, first spot (gray) moves from position 1 to position 5 during time duration $T_0$ to $T_n$. There are positions between adjacent scan positions. For instance, second spot (black) scans from position 9 through position 13 during time duration $T_0$ to $T_n$. Accordingly, positions 6 through 8 remain unscanned or blank during this time duration although a subsequent scan would typically be performed to scan these previously unscanned positions. Each sweep can be produced, for example, by the AOD that generates the initial beam sweep and the DOE that multiplies the initial beam sweep, for example, into three sweeps. As shown, the three spots sweeps are each represented by a corresponding scan boxes 332a, 332b, 332c, respectively.

FIG. 3C shows the sweep positions for all three spots under high magnification. In this example, three smaller sized sweep boxes 334a, 334b, 334c are produced under high magnification. Although the magnification of each spot may change, the DOE 311 that is placed after the magnification changer 307 causes each scan box to have a same center position for different magnifications. FIG. 3D illustrates the relative sweep positions for both low and high magnification. For instance, while a high magnification first spot (gray) would be scanned from position 2 to position 4, a low magnification spot (gray) would be scanned from position 1 to position 5. As shown, the low magnification scan boxes 332a~332c have the same center as the high magnification scan boxes 334a~334c. If the collection area corresponds to the largest scan boxes (e.g., 332a~332c) for the lowest magnification, both the low and high magnification spots may be separately imaged by the collection optics.

Figure 4:
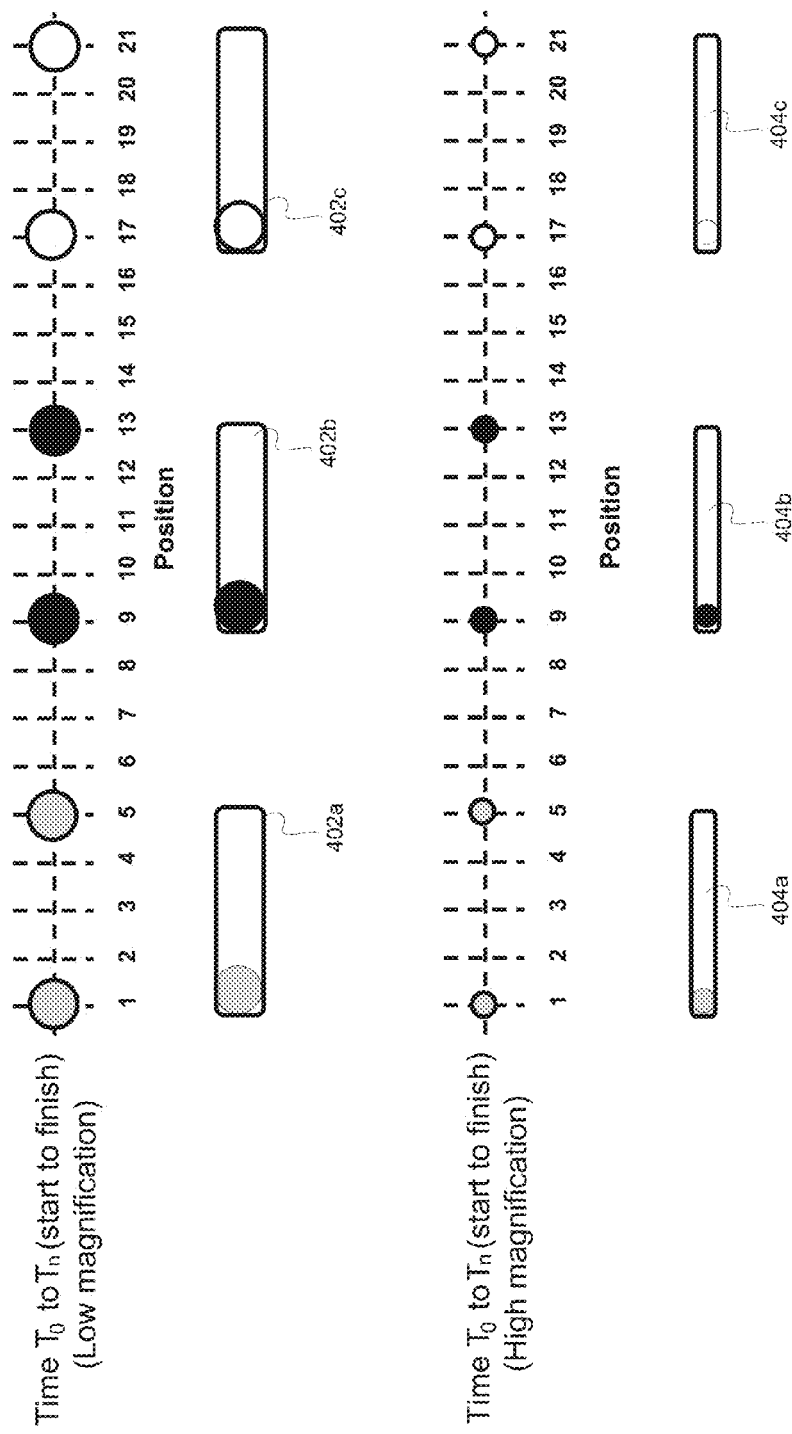
FIG. 4 illustrates sweep positions for low and high magnification spots having a same scan length in accordance with a second implementation.

In a further embodiment, the entire length of the AOD may be used for high magnification, while only a portion of the AOD's length is used for lower magnifications. FIG. 4 illustrates sweep positions for low and high magnification spots having a same scan length in accordance with a second embodiment. As shown, the positions of both the high and low magnification sweeps are the same. For instance, both low magnification and high magnification first spots (gray) scan from position 1 to position 5, and result in same length scan boxes 402a and 404a, respectively. Likewise, both low magnification and high magnification second spots (black) scan from position 9 to position 13, and result in same length scan boxes 402b and 404b, respectively. Both low magnification and high magnification third spots (white) scan from position 17 to position 21, and result in same length scan boxes 402c and 404c, respectively. This embodiment more efficiently covers the segmented scan line under variable magnifications.

Figure 5A:
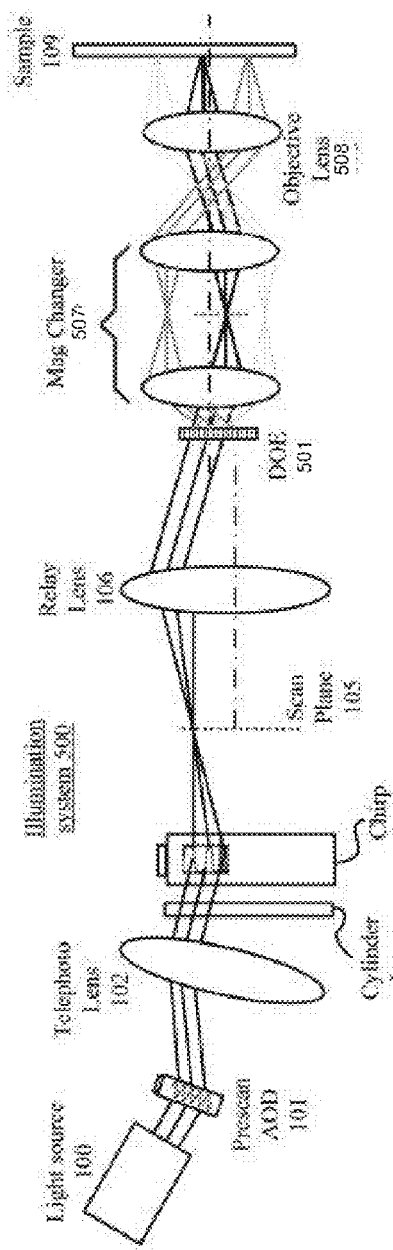
FIG. 5A illustrates an exemplary AOD illumination system that can generate multiple scanning spots without flood illumination of the AOD.

FIG. 5A illustrates another exemplary AOD illumination system 500 that can generate multiple spots without flood illumination. Both FIGS. 3A and 5A are simplified diagrams and do not show every component that may typically be present in such a system so as to simplify the description. For instance, there may be a relay lens located between the DOE and objective lens. When the pupil of the illumination system is physically located at the objective and inside the lens assembly, a relay is typically used to form a real pupil outside the objective so that the DOE may be placed at such pupil. For low numerical aperture systems, the physical stop location will be outside the objective lens assembly. For high numerical aperture systems the physical stop may be located within the objective lens assembly. In this case, an additional relay would be added to the system to provide a location to place the DOE.

Figure 5B:
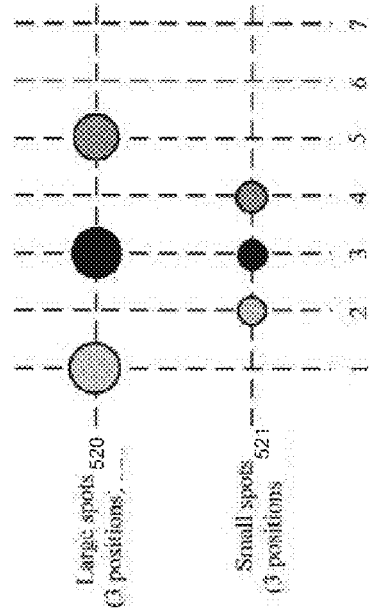
FIG. 5B illustrates the effects of changing the magnification of the illuminator using the magnification changer on the spot size, spot spacing, and scan length on a sample for the illumination system shown in FIG. 5A.

In the embodiment of FIG. 5A, a diffractive optical element (DOE) 501 can be positioned before magnifier changer 507 to generate a plurality of spots. Although FIG. 5A shows three spots being generated, other embodiments can generate a different number of spots. FIG. 5B illustrates the effects of changing the magnification of magnifier changer 507 on the spot size, spot spacing, and scan length on sample 109 for illumination system 500. Note that the different fill grayscale levels indicate different spots (and correspond to the different line grayscale levels of FIG. 5A). As shown in FIG. 5B, large spots 520 have spacing associated with three positions 1, 3, and 5, whereas small spots 521 have spacing associated with three positions 2, 3, and 4. The spot positions for both low and high magnification spots in FIG. 5B represent the center scan position for each spot.

Having high and low magnification scan segments with overlap makes appropriate isolation for the scattered light from the multiple spots more difficult. For example, FIGS. 6A and 6B illustrate exemplary sweeps of three small spots 601, 602, and 603 (corresponding to those shown in FIG. 5B) between times $T_1$ and $T_4$. FIG. 6B represents the scans of spots 601, 602, and 603, as boxes of the same grayscale level, wherein the boxes represent the paths of the spots as a result of the propagation through the chirp AOD. FIG. 6B shows that there is an overlap of the colinear scans of different spots (which would occur for both the big spots and the small spots). This overlap will result in undesirable spot crosstalk.

Figure 7B:
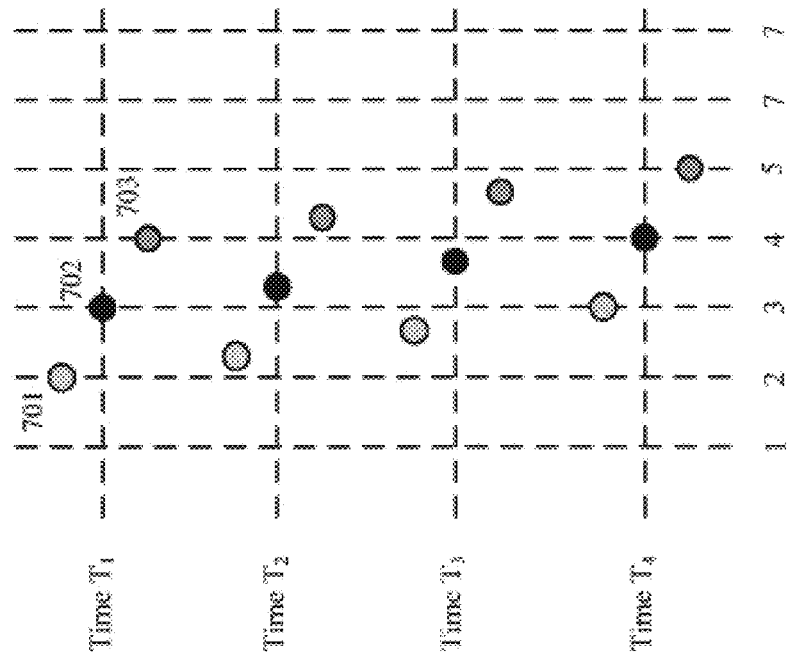
FIGS. 7A through 7C illustrate how a prism can be used in conjunction with an illumination system to create an appropriate isolation of spots in the collector optics.
Figure 7A:
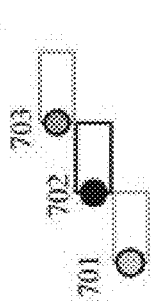
Figure 7C:
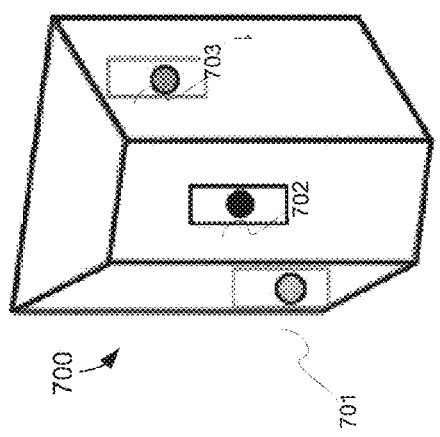

To provide the isolation between spots, thereby minimizing crosstalk, additional optics and techniques can be used. In one example, shown in FIGS. 7A through 7C, a prism 700 can be used in a collection system to isolate spots that are staggered in the stage propagation direction by the illumination optics. FIG. 7C is the prism that is located in the collection optics. U.S. Pat No. 7,075,638, issued to Kvamme on Jul. 11, 2006, and incorporated by reference herein, describes such an illumination and collection system. In this system, prism 705 and additional optics, such as a spherical aberration correction lens and a transmitted lens, can be positioned such that scattered light from the plurality of spots, e.g. beams associated with spots 701, 702, and 703 (FIG. 7A), on the sample are directed to a specific facet of prism 705, as shown in FIG. 7C. In turn, prism 705 directs each beam to a separate detector. FIG. 7B shows the scan sweeps of spots 701, 702, and 703 during operation of the associated inspection system. Prism 705 (which is part of the collector) takes advantage of an offset shown in FIGS. 7A through 7C (the offset being generated by a grating, which is part of the illumination system) to desirably increase the spot isolation. Thus, referring back to FIG. 7A, turning a grating will result in spots 701, 702, and 703 (and their associated scans) no longer being co-linear along the scanning axis (e.g., they will instead form 3line segments staggered in the XY stage propagation direction).

The prism in the collection optics may work for a range of magnifications (not fixed), even if there is no collection side magnification changer. However, the center scanning spot (702) will remain fixed and the side spots (701 and 703) will creep up and down the facets of the prism (in addition to changing size and length of the scan boxes) as magnification changes if there is no magnification changer in the collection side. If there is a magnification changer in the collection channel that changes with the illumination magnification, the images of the spots on the prism can remain constant.

Although the illustrated prism 705 works well under certain applications, the prism approach is only capable of supporting a limited number (e.g., 3) of illumination spots. Additionally, this system's illumination only works well with normal and near normal angles of incidence and does not work with highly oblique angles of incidence, in which the objective is tilted relative to the sample (or visa versa). Oblique angled incident beams that are scanned across the sample will tend to have some of the spots not be positioned in the focal plane (unfocused) due to the staggering of the spots (e.g., FIG. 7A). Although an extremely large NA (numerical aperture) objective lens may be used to achieve oblique angles without tilting, a large NA lens has significant associated costs.

The accurate detection of defects on a sample surface depends on the correct measurement and analysis of each spot in the scan independently. Therefore, a need arises for optimizing techniques and systems using spot scanning techniques such as AODs that ensure the isolation of these spots, thereby minimizing crosstalk, while minimizing system complexity and cost.

Example System Embodiments

In contrast to systems that have the objective axis perpendicular to the image plane, certain embodiments of the present invention include a longitudinal imaging system having imaging and non-imaging optics with an optical axis that is parallel and coincident with the sample plane or image plane. That is, the illumination spots are imaged along the optical axis of the collection system, rather than in a plane that is perpendicular to the optical axis of the collection system.

Figure 8:
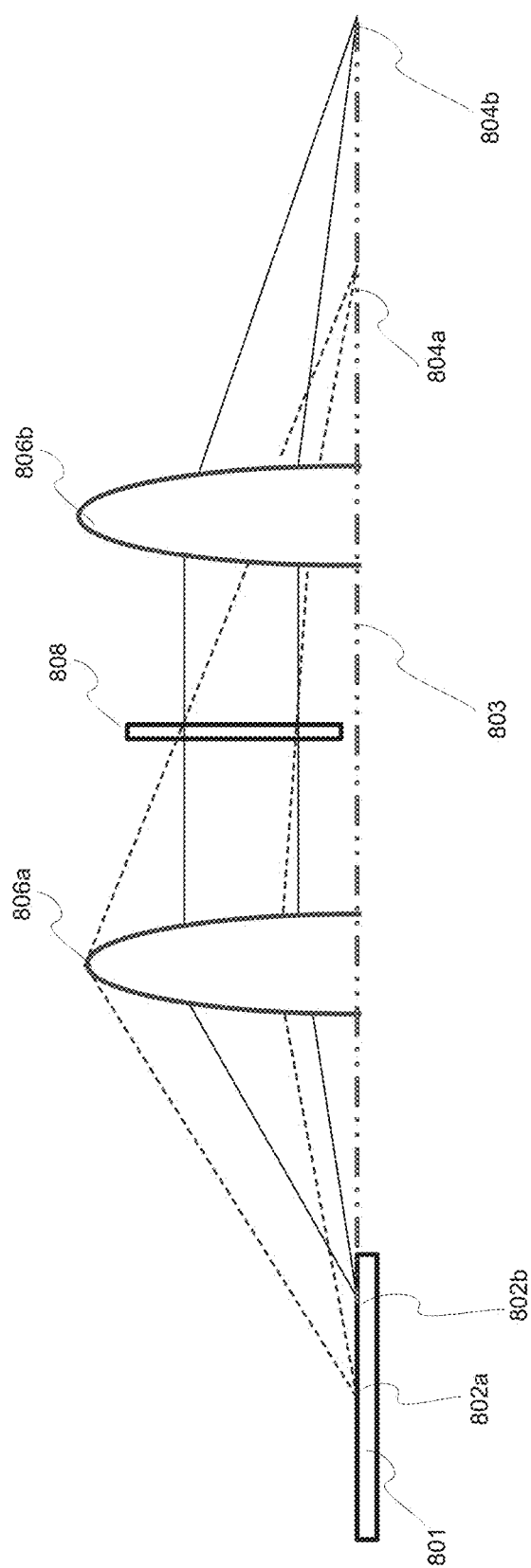
FIG. 8 is a general diagrammatic representation of longitudinal imaging of objects.

FIG. 8 is a general diagrammatic representation of longitudinal imaging of multiple objects. As shown, two spots 802a and 802b that are scanned on the surface of sample 801 are imaged parallel to the optical axis 803 of lens 806a and 806b. The lens 806a and 806b may start as whole lens that are subsequently cut (e.g., in half or more) so that the sample does not run into the lens as the sample moves. The optical axis 803 of the lens 806a and 806b is coincident with the wafer surface and illumination scanning spots. Resulting image objects 804a and 804b are collected by this longitudinal system.

In certain embodiments, the illumination optics are configured such that the scanning spots are positioned to all lie along a single line with the spots interleaved (e.g., line-blank-line-blank, etc.). The optical axis of the illumination objective can be tilted and still have all the spots in focus because they all lie and remain along a single line. The side collector is tilted such that its optical axis is the line formed by the scanning spots of the illumination optics. As viewed from the optical axis of the collector, the spots from the illumination optics would be scanning away or toward the observer, rather than left to right or up or down.

FIGS. 9A~9E are diagrammatic representations of an inspection system 900 with longitudinal imaging in accordance with one embodiment of the present invention. Although this system 900 is described as having two incident channels for generating normal and oblique incident beam scanning spots and three detection channels for detecting light from normal and two longitudinal side channels, the system 900 may include any suitable number and type of incident and collection channels, including at least one longitudinal collection channel. Additionally, although each channel is illustrated with respect to three scanning spots, each incident channel may generate any number of scanning spots and each detection channel may detect light from any suitable number of scanning spots. The system may generate 3 or more spots. In specific alternative implementations, 9, 15, 30, etc. spots are generated from a normal and an oblique angle and light is collected from a normal and two or more longitudinal side channels. Each spot may have any suitable shape, such as circular or elliptical.

Figure 9A:
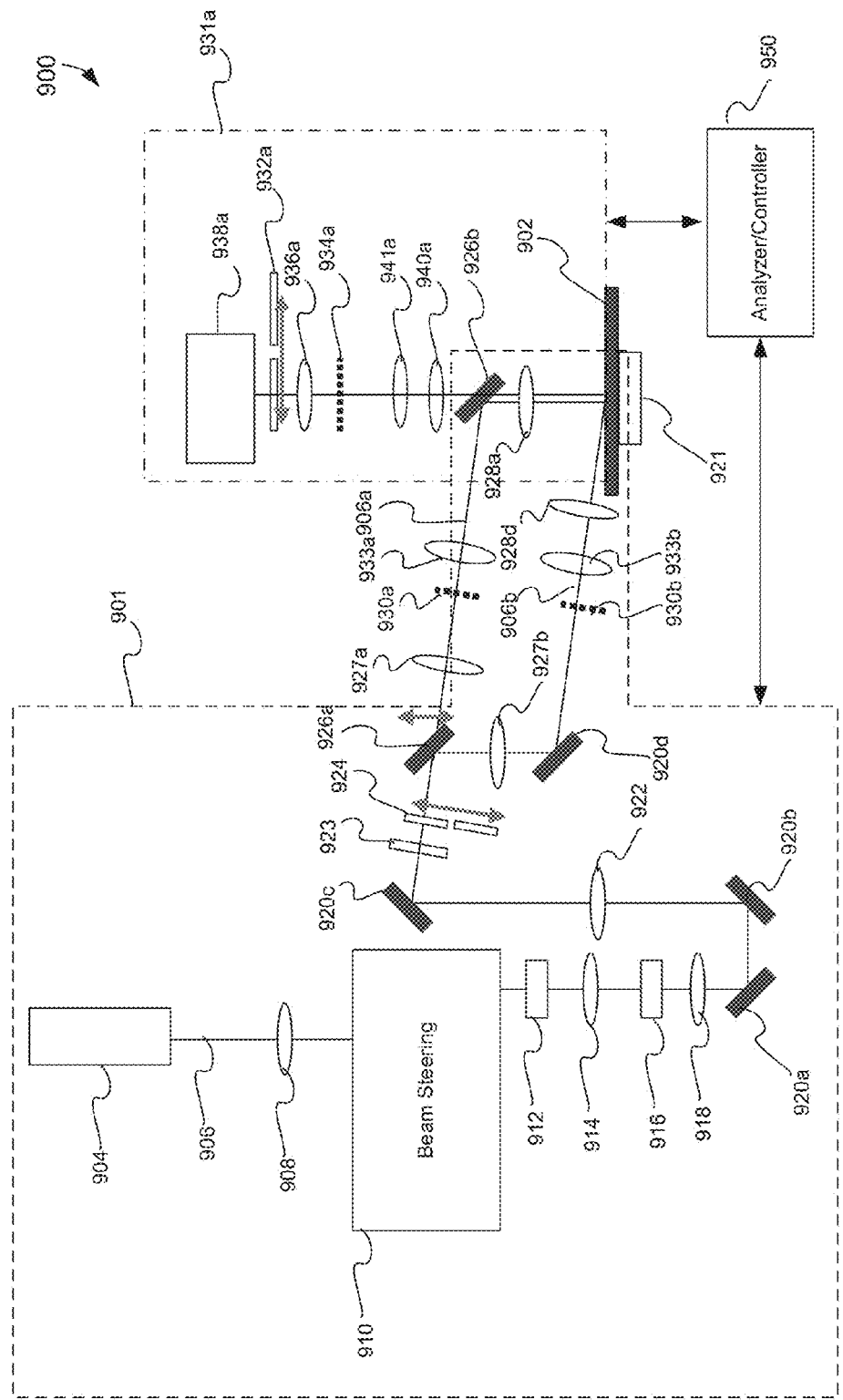
FIGS. 9A~9E are diagrammatic representations of an inspection system with oblique and normal incidence and normal collection and longitudinal side collection channels in accordance with one embodiment of the present invention.

FIG. 9A is a side view of an inspection system 900 in accordance with one embodiment of the present invention. In general, the inspection system 900 may be utilized to inspect a sample 902 for defects or measure characteristics, such as critical dimension (CD) or film thickness, on the sample 902. The sample surface 902 may be smooth or patterned.

The view of FIG. 9A shows an illumination system 901 for generating normal and oblique incident beams and a normal collection channel 931a for collecting light that is reflected normal and near normal to a sample surface 902. However, the system 900 also includes two longitudinal side collection channels that are not shown in this side view of FIG. 9A, but such side channels are illustrated in FIGS. 9D and 9E.

Figure 9C:
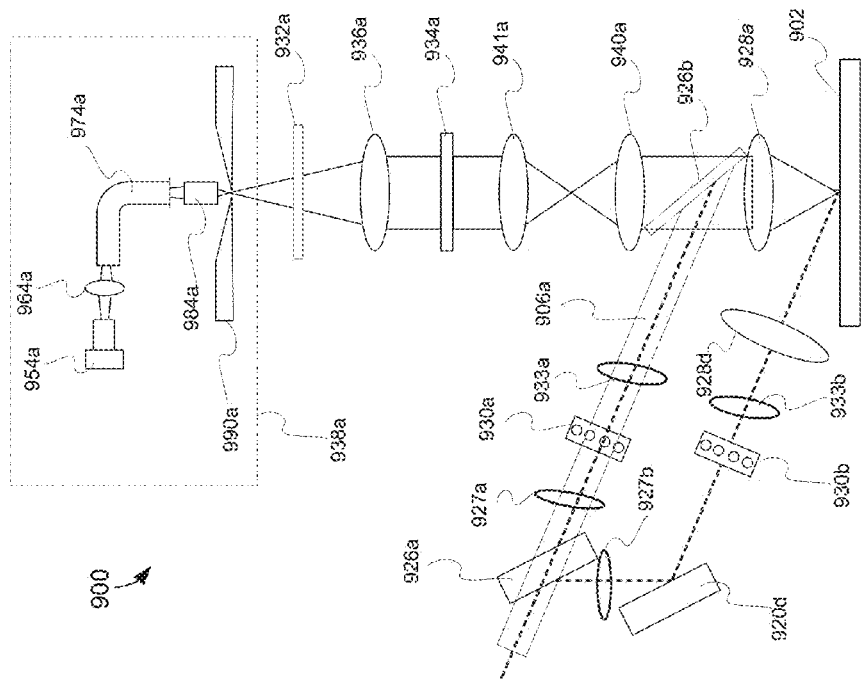
Figure 9B:
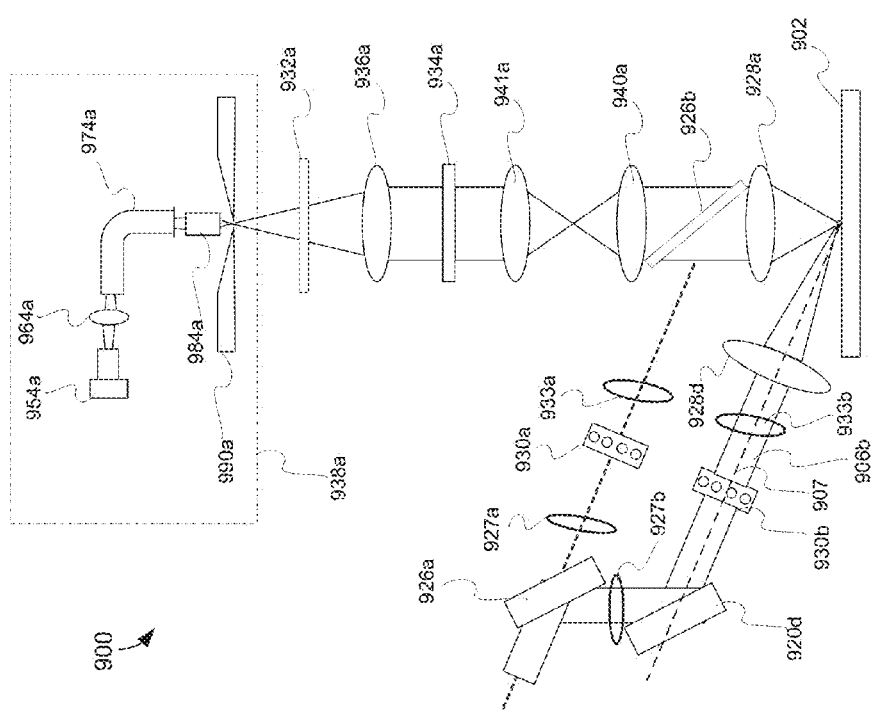
Figure 9D:
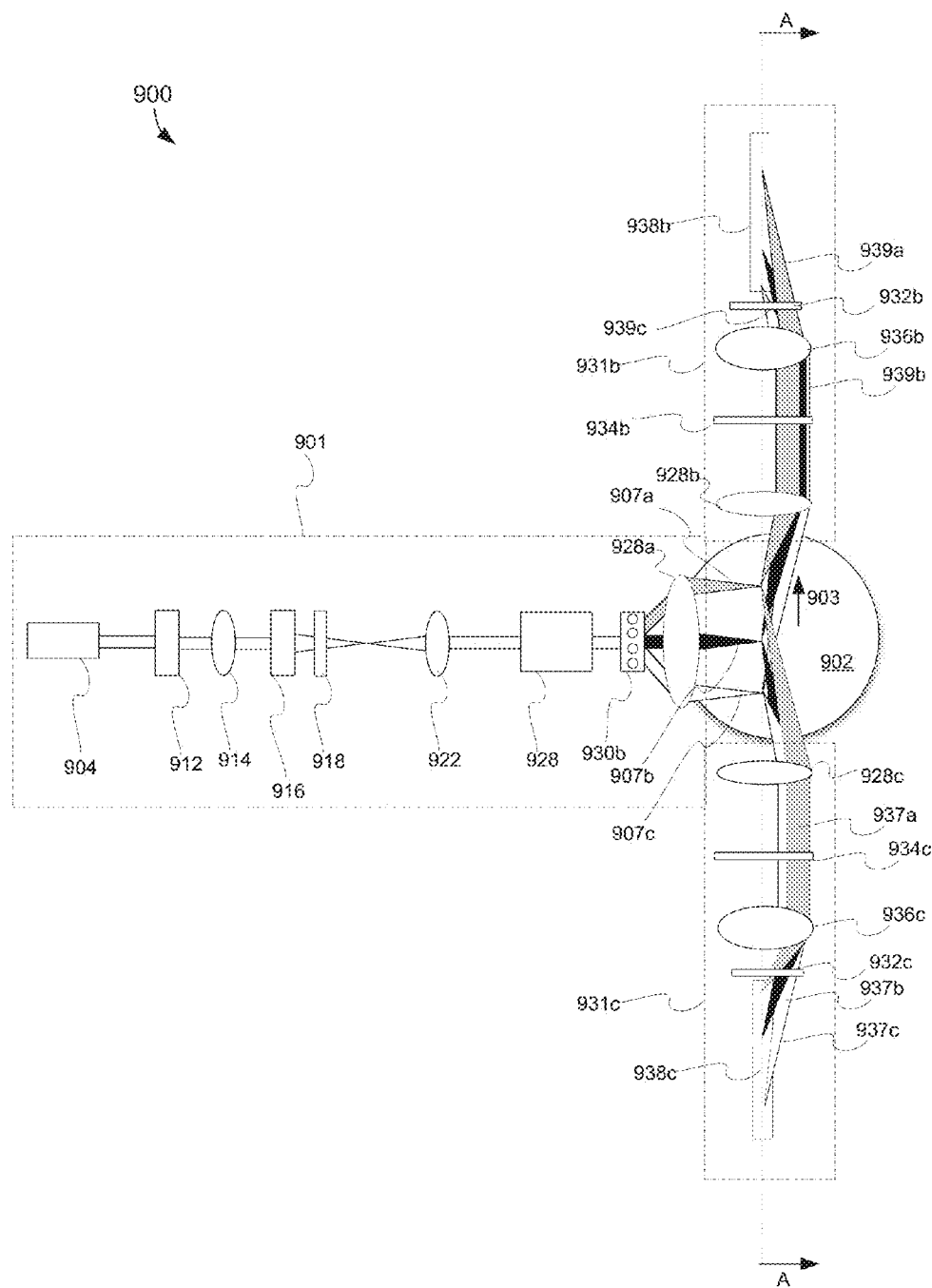
Figure 9E:
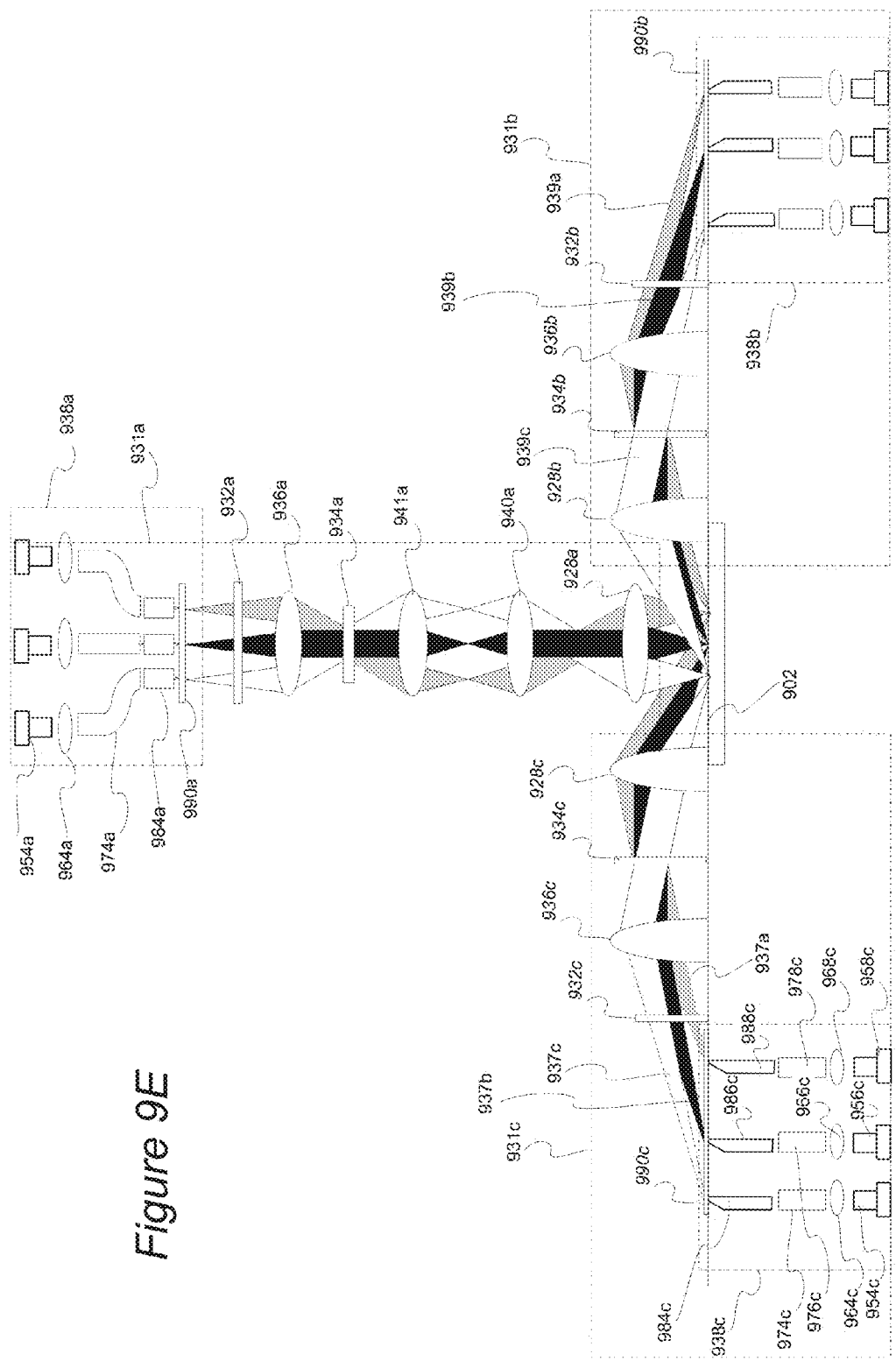

FIG. 9B illustrates normal collection resulting from oblique incident light, while FIG. 9C illustrates normal collection resulting from normal incident light. FIGS. 9B and 9C are more detailed diagrammatic side views of the inspection system 900. However, only a single normal output beam is shown for simplifying the description of normal collection. In contrast, FIG. 9E illustrates a front view of the normal collection and longitudinal side collection of three beams.

The illumination system 901 includes one or more light sources for generating the scanning beams. As shown in FIG. 9A, a light source 904 (typically, a laser) emits a beam 906. The wavelength of the illumination beam 906 depends on the particular requirements of the application. For example, the illumination beam 906 has a wavelength of about 266 nm. Beam 906 can be produced by any suitable light source, such as a DPSS (diode pumped solid state) CW (continuous wave) DUV (deep ultraviolet) laser.

Beam 906 may be directed through zoom optics element 908, which compensates for laser beam changes in size, and the beam 906 then impinges on beam steering system 910 for aligning the beam on a particular axis having additional illumination elements, such as pre-scan AOD 912, telephoto lens 914, Chirp AOD 916, and cylinder lens 918. The illumination optics may include additional lenses, cylindrical lenses, waveplates, filters, and one or more air slits.

The illumination path may include other optical elements, such as a relay lens 922 for collimating the incident beam, analyzer 923 for polarization, waveplates 924 for providing any linear or circular polarizations (e.g., S, P, etc.), and any number of mirrors (e.g., 920a~d) and beam splitters (e.g., 926a and 926b) for forming both normal and oblique incident beams. In alternative embodiments, element 926a is replaced with a beam splitter, prism and/or mirror assembly. Any of the mirrors or beam splitters may be movable (e.g., actuated mirror/splitter 926a).

Any number of mirrors and beam splitters may be used to form multiple incident paths. As illustrated, the incident beam 906 is transmitted through beam splitter 926a, towards magnification changer assembly 927a, which is configured to change the magnification of the normal incident beam prior to it being incident on DOE 930a, which is configured to form multiple beams 906a, which are reflected from mirror/beam splitter 926b and focused onto sample 902 via objective 928a, which doubles as a collector lens. The normal path may also include a relay lens 933a for generating a real pupil at the pupil plane at which DOE 930a is placed.

The illumination system 901 may include components for forming one or more oblique incident beams. For instance, beam splitter/mirror/prism 926a reflects a portion of the incident beam towards magnification changer assembly 927b, which is configured to change the magnification of the oblique incident beam prior to it being incident on reflecting mirror 920d. DOE 930b generates multiple oblique incident beams 906b that are focused by objective 928d onto sample 902. The illustrated 3×1 DOE elements for generating multiple beams may be replaced by any suitable DOE or, more generally, any n×m DOE. The oblique path may also include a relay lens 933b for generating a real pupil at the pupil plane at which DOE 930b is placed The optical axis (907 in FIG. 9B corresponds to one oblique beam) of each oblique incident beam (906b) may be directed onto the wafer surface 902 at an angle θ. This angle θ may be in the range of 10-85 degrees with respect to the normal to the sample surface 902, depending on the particular application. Multiple oblique angles may be achieved by translation of component 920d. Incident oblique light comes in at an oblique angle from a tilted objective 928d.

Referring back to FIG. 9A, the scanning mechanism includes the chirp AOD 916 and the translation or sample stage 921, upon which the wafer or sample rests. The position of the wafer on the stage 921 may be maintained in any convenient manner, e.g., via vacuum suction. Inspection is achieved by scanning the chirp AOD 916 in one direction (referred to as the fast scanning direction) while moving the stage 921 in an orthogonal direction (referred to as the slow scanning direction). This produces a ribbon like shape of inspected area per illumination spot. The stage 921 then steps to a new uninspected area and repeats the process (filling in the blank) as described below.

Each illumination optics spot may be moved with respect to the stage so as to direct light to the sample and/or the stage moved relative to each collection channel, including one or more detectors or cameras, so as to collect light from the sample by any suitable movement mechanism. For example, a motor mechanism may be utilized to move the stage or any other component of the system. Each motor mechanism may be formed from a screw drive and stepper motor, linear drive with feedback position, or band actuator and stepper motor, by way of examples.

The illustrated system 900 also includes normal collection channel 931a which can be used to collect scattered light from the oblique incidence illumination mode, as well as specular or BF (brightfield) and scattered light from the normal incidence illumination mode. Light directed at the channel in the normal and near normal direction may be transmitted through lens 928a, beam splitter/mirror/prism 926b, lenses 940a and 941a, Fourier filter and configurable aperture assembly 934a, lens 936a, and polarization analyzer assembly 932a and be directed towards sensor module 938a.

The normal collector channel 931a may collect light over a fixed solid angle over a region which is approximately perpendicular to the plane of the wafer. The normal collector may be used to collect scattered light from the intentional patterns on the wafer, as well as to detect defects which scatter light in an upwards direction. Signals collected from the intentional patterns may be used to facilitate the alignment and registration of the wafer pattern to the coordinate system of the mechanical stage in the instrument.

Figure 9F:
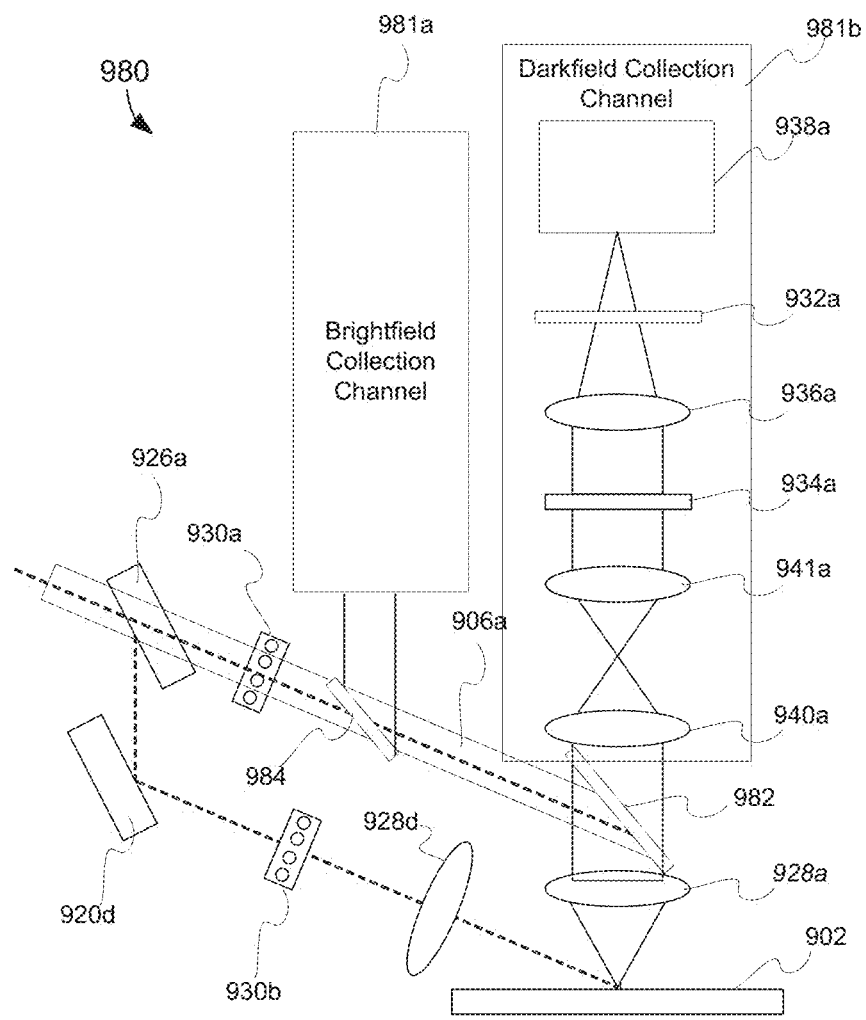
FIG. 9F is a side view of a portion of a system having separate brightfield and darkfield collection channels in accordance with an alternative of the present invention.

FIG. 9F is a side view of a portion of a system 980 having separate brightfield and darkfield collection channels in accordance with an alternative of the present invention. The system can have similar components as the system 900 of FIGS. 9A through 9E. However, the system 980 may include any number of optical elements for directing the specular brightfield light and the scattered darkfield light that emanates from the sample towards separate collection channels. For instance, mirror 982 may have a center reflective portion that reflects the normal incident beams towards the sample and also reflects the specular reflected output light from the sample towards mirror 984, which reflects such brightfield light towards brightfield collection channel 981a. The mirror 982 may also have transparent side portions that transmit the scattered and diffracted light from the sample 902 towards a darkfield collection channel 981b. The darkfield and brightfield collection channels may have similar components as described herein. Alternatively, these collection channels may share one or more components.

As shown in both FIGS. 9B and 9C, light that is reflected or scattered from the surface in the wafer surface normal or near normal direction is collected and collimated through lens assembly 928a. Lens assembly 928a may include multiple optical elements so as to produce a real accessible collection pupil. This collimated light may then be transmitted through optical element 926b and then through lens 940a and 941a, which may be configured to relay the collected light towards a Fourier plane. Fourier filter and flexible aperture mechanism 934a may be configured to spatially filter portions of the output light at the Fourier plane. In addition, mechanism 934a may include a programmable aperture system for transmitting various spatial portions at the Fourier plane to maximize signal and/or minimize noise (and resulting angles with respect to the normal optical axis) of the output beam.

The output normal beams may then be focused by lens 936a through polarization analyzer 932a onto sensor module 938a. Only a portion of each sensor module 938a is shown for a single normal output beam. As shown, the sensor module 938a may include a spot or beam separation assembly having a slit 990a and prism assembly 984a for separating each output beam. As shown, each spot passes thru the slit 990a and then into a prism 984a. The prism 984a is used to both separate the spots and homogenize the light. The output light for each beam may then be output from its corresponding prism (984a) onto a fiber optics element 974a for passing the output beam towards focusing element 964a, which focuses its output beam onto a sensor (954a). Fiber optics element 974a provides further homogenization of the beam and enables the output to be directed onto a separate sensor 954a for each spot. The function of the fiber could also be accomplished using mirrors, prisms or the like. Each fiber randomizes the received output light. As described further below, other isolation mechanisms may be used, besides utilizing a slit, prisms, and/or optical fibers.

FIG. 9D illustrates a top view of the system 900, including the oblique incident channel of the illumination system 901 and side collection channels 931b and 931c. As shown, the oblique incident channel generates three oblique incident beams 907a (gray), 907b (black), and 907c (white) on sample 902. The three incident beams may be swept across the sample, for example, in direction 903. In response to these incident beams 907a~907c, output beams that are scattered, diffracted, or reflected from the sample may be collected by side channels 931b and 931c. As shown, the side collection channels 931b and 931c have an optical axis that is parallel to the scan direction 903 of the oblique illumination subsystem.

It is noted that the side collection channels are both shown to be perpendicular to the oblique incident channel, as viewed from the top in FIG. 9D. For instance, if the oblique incident system 901 was defined to be positioned at a yaw angle of 180°, collection channel 931b is positioned at 90° and collection channel 931c is positioned at 270°. The longitudinal collectors can be configured to collect light +/−20-80 degrees (e.g., 65 degrees) in azimuth and 20 to 80 in elevation. It is noted that only a small portion of each side output beam's cone is shown in FIG. 9D and 9E so as to more clearly show each beam's relative path.

The system may also include any number of side collection channels, besides the illustrated two side channels that have an opposite yaw angle. For instance, the system can include more than one pair of opposite side channels. In another example, the system may include any number of side channels that each do not belong to a pair of opposite angle side channels.

As shown, each side collection path may include a front lens or lens group (928b or 928c) for receiving the output beams that are scattered from the sample 902 and directing such beams towards a position at which a Fourier filter, programmable aperture or apodization element (934b or 934c) is placed. The output beam may then be directed towards a rear lens or lens group (936b or 936c), which may then direct the output beam through a polarization analyzer element (932b or 932c) to be focused onto a sensor module (938b or 938c), which are described further below with respect to FIG. 9E. The polarization analyzer elements (932b and 932c) may be configured for selectively capturing any polarization scattered, diffracted, or reflected from the sample 902.

Figure 9E is a diagrammatic side view of the system 900 of FIG. 9D as viewed in direction A-A. This illustration also shows the normal collection channel 931a, but does not show the illumination channel 931c. As shown, the front lens (928b and 928c) and rear lens (936b and 936c) are in the form of half lenses although they may be any suitable portion of a whole lens so as to collect obliquely scattered, diffracted, reflected light along a longitudinal axis with respect to the sample.

Each collected side beam is focused to impinge on a sensor module (938b or 938c). Each sensor module (938b or 938c) may include a spot separation mechanism including the slit assemblies (990b or 990c) and prism components (984c, 986c, and 988c) for separating the different output beams (937a~c or 939a~c) into separate receiving prisms. As shown, sensor module 938c includes three prisms 984c, 986c, and 988c for separately receiving three output beams. The output beams bounce within each prism to be output towards a corresponding fiber optics module (e.g., 974c, 976c, or 978c), which then directs the corresponding output beam towards a focus lens (e.g., 964c, 966c, or 968c), which then focuses the corresponding output beam onto a sensor (e.g., 954c, 956c, or 958c). Each sensor can take the form of a PMT, avalanche photodiode, pin diode, CCD camera, etc.

Sensor module 938b may have similar components as sensor module 938c. Likewise, the normal collection sensor module 938a may include similar components, such as slit assembly 990a, three prisms (e.g., 984a), three fiber optics elements (e.g., 974a), three focus lens (e.g., 964a), and three sensors (e.g., 954a).

Mechanisms for increasing dynamic range of the detected signals may be provided in proximity to collector channels. In general terms, a high dynamic range collector includes a light sensor, such as a photomultiplier tube (PMT), for generating a signal from detected photons and an analog to digital converter (ADC) for converting the light signal to a digital light signal. Of course, other suitable mechanism may be used for sensing light and converting an analog signal into a digital signal. A gain adjustment feedback system may also be used to adjust the gain of each PMT.

It is noted that the illustrated system 900 includes illumination magnifier changers (927a and 927b), while excluding a collection magnifier changer. In other words, the system 900 has a fixed collection magnification, which simplifies and lowers the cost of the system. When the illumination magnification is increased, as described above, the spot size and scan velocity are decreased. Although decreased spot size corresponds to increased sensitivity, decreased velocity corresponds to lower throughput. In the illustrated system 900, the oblique illumination DOE 930b is placed after the illumination magnifier 927b (and there is similar placement between the magnifier 927a and DOE 930a in the normal incident channel). This DOE 930b placement allows the magnified spot to have a same center position, regardless of the spot's size change. Although the nominal centers of each scan line is the same with different magnifications, the scan length changes. As described further above, this position of the DOE 930b ensures that the center scan position for all the spots is unchanged with changes in illumination magnification. Spot size and velocity, however, do change with illumination magnification changes. A large AOD can also be used to provide scanning in only a center portion of the AOD for a large spot, while providing scanning across the entire AOD for a smallest spot as further described above.

FIG. 10A is a diagrammatic side view of a spot separator assembly having a slit and prisms for receiving output beams from multiple illumination areas in accordance with a specific implementation of the present invention. In this example, the spot separator assembly is a pair of razor blades having a first edge portion 1002a and a second edge portion 1002b which together form a gap or slit 1002c. Each output beam may be focused to a point 1004a that is within this gap. A single output beam 1004 with a focus point 1004a is shown in FIG. 10A although the system will typically be configured to collect and isolate the scattered, diffracted, and reflected light from multiple, simultaneous scanning spots.

FIG. 10B is a diagrammatic representation of the spot separator and prisms as viewed in direction B-B of FIG. 10A. As shown in both FIGS. 10A and 10B, the output beam forms a cone that focuses to a point 1004a that is positioned where the razor edge portions 1002a and 1002b have a narrowest width in gap 1002c. The output light 1004 passes through the razor gap 1002c and goes out of focus to then fill prism 1006a. In one embodiment, each prism has a side that is adjacent to the bottom of the razors 1002a and 1002b. Each output beam separately fills a particular prism and then is output from the prism to an adjacent fiber optics element (984c of FIG. 9E). That is, individual prisms are positioned to capture individual scan spots. In one embodiment, there are 9 prisms for each channel positioned behind the slit 1002c.

Additionally, the position of the prisms or apertures may be adjustable to accommodate for distortion (illumination or collection optics induced) of the inspection system, which causes the spacing between the spots as viewed by the sensor modules 938a, 938b, and 938c to be non-uniform.

Prism and razor blade alternatives may include a DOE, such as a reflective or transmissive grating, under each collected spot position in place of each prism, to reflect or transmit the output light for each spot to a corresponding fiber optic and/or sensor. Each grating or set of gratings would include a set of diffractive features for diffracting light from the imaged spots towards the sensor, whereas light between the spots (and between the diffractive patterns) is not diffracted towards the sensors. In another example, a substantially opaque printed pattern may be formed on a substantially transparent substrate(s) to form a slit. For instance, the printed pattern may be formed from a coating, which is deposited on a glass substrate.

The collections channels may alternatively or additionally include a series of mirrors for providing randomization of the collected light. For instance, each prism may be replaced by a series of mirrors. One or more mirrors may be placed in a position that corresponds to each prism facet (e.g., 1020a, 1020b, 1020c, and 1020d). Optical fibers or a combination of mirrors and fibers may also replace the prisms.

Figure 10C:
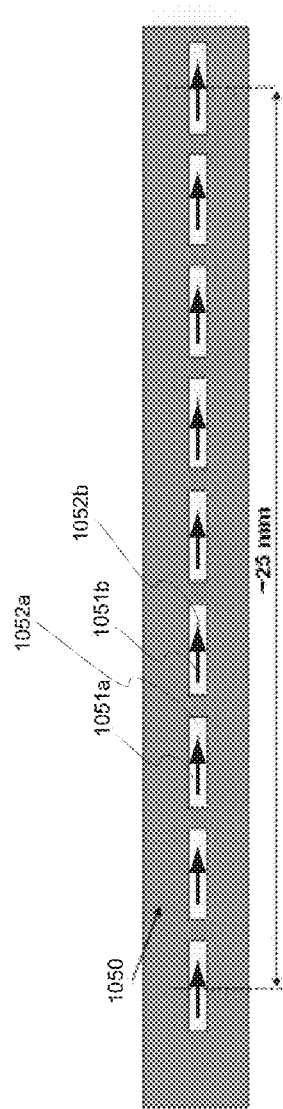
FIG. 10C is a diagrammatic representation of a mask type spot separator in accordance with a specific implementation of the present invention.

Other suitable spot separators may include a mask with slits for the individual scanned spots. FIG. 10C is a diagrammatic representation of a mask type spot separator 1050 in accordance with a specific implementation of the present invention. For example, the mask can be formed from a foil material with apertures (e.g., 1052a and 1052b) that are each shaped to enclose a single spot scan (e.g., 1051a and 1051b). For instance, a prism may sit beneath each aperture (e.g., 1052a, 1052b). The mask separator may replace the razor portions and optionally combined with prisms, fibers, and/or mirrors as described above. One or more masks can be positioned in each channel.

A grating may be added to the mask of FIG. 10C to diffract the light from each spot into a prism or fiber or other collection assembly. FIG. 10D is a diagrammatic representation of a mask type spot separator with gratings in accordance with an alternative embodiment of the present invention. A top view of the mask 1056 and a side view of the mask 1058 are shown. Each aperture has gratings (e.g., 1054a and 1054b). In this example, the gratings are aligned vertically across each aperture (as seen from top view 1056) so as to diffract the incoming light (e.g., 1046a) in a down direction into each prism, as opposed to the next prism. For instance, incoming spot light 1046a is diffracted by grating 1054a down into prims 1048a. The grating can be reflective (diffract light up) or transmissive (as shown).

FIG. 10E illustrates a top view of a mask type spot isolator with gratings that are oriented in different directions in accordance with another embodiment of the present invention. For example, aperture 1060a has a vertical grating; aperture 1060b has an angled grating; and aperture 1060c has an inversely angled grating. These different grating orientations diffract light down/up, down/up to the left, or down/up to the right.

Figure 10F:
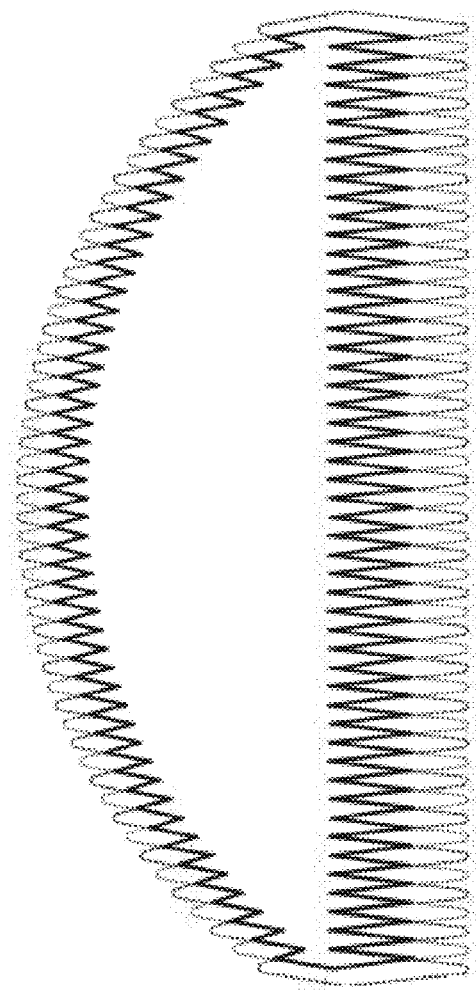
FIG. 10F is a diagrammatic representation of an aperture having serrated teeth and is formed from two masks with serrated teeth in accordance with one embodiment of the present invention.
Figure 10G:
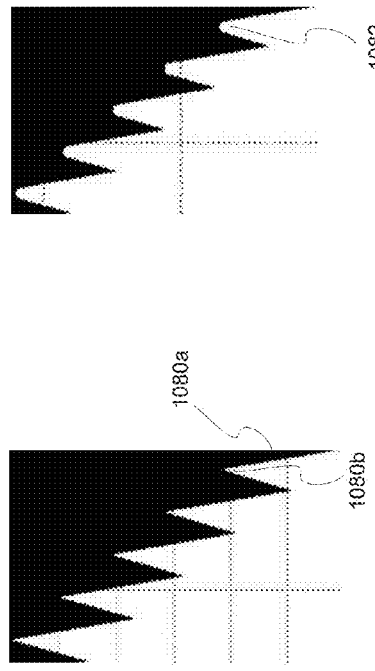
FIG. 10G shows both ideal and non-ideal aperture teeth.

An apodization mechanism may be added to the aperture assembly (934a~934c) to control diffraction and, thus, spot-to-spot crosstalk. FIG. 10F is a diagrammatic representation of an aperture having serrated teeth and is formed from two masks with serrated teeth in accordance with one embodiment of the present invention. FIG. 10G shows both ideal and non-ideal aperture teeth. Ideally, the aperture teeth would have sharp vertical points (1080a) and dips (1080b) to diffract the light away from the optical axis (e.g., to the left and right, rather than forward). However, the fabrication of the aperture teeth may result in rounded portions, such as dip 1082, which would diffract some unwanted light towards the prisms. As shown in FIG. 10F, a first mask (dotted line) having rounded dips may be overlaid with a second mask (dashed line) also having rounded dips. The supposition of the two masks is the solid line that has sharp non-rounded features. In the longitudinal collection channels, the teeth may be oriented perpendicular to the optical axis and in a plane that is parallel to the wafer surface normal. In the normal collection channel, the teeth may be perpendicular to the optical axis and in a plane that is perpendicular to the wafer surface normal.

Any suitable type of apodization mechanisms may be utilized at each aperture stop. Variable transmission coatings can be deposited onto a transparent substrate, such as glass, to provide apodization. Different patterns (e.g., dots, triangles) may be printed so as to form graduated densities at the edge of the aperture. Different densities of the printed patterns may transmit, reflect, or diffract light to perform apodization in the aperture. All printed patterns and coatings may be formed to provide a variety of transmission profiles (linear, cosine, Gaussian, etc.) that can be utilized to control crosstalk. Several apodization techniques and mechanisms are further described in U.S. Pat. No. 5,859,424 issued 12 Jan. 1999 by Adam E. Norton et al., which patent is incorporated herein by reference in its entirety.

Figure 10H:
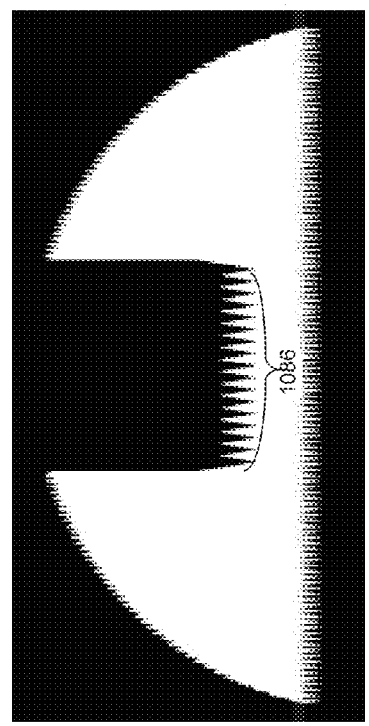
FIG. 10H illustrates a Fourier filter in the form of closely spaced pin-like structures that can be dropped down across the aperture to block particular portions of the light in accordance with one embodiment of the present invention.

A Fourier filter may also be placed at the aperture stop of each collection channel so as to block particular diffraction spots or noise or to isolate certain signals. The Fourier filter can be configured to selectively block portions of the light at the aperture stop. FIG. 10H illustrates a Fourier filter in the form of closely spaced pin-like structures that can be dropped down across the aperture to block particular portions of the light in accordance with one embodiment of the present invention. As shown, pins 1086 are dropped into the aperture to block a corresponding portion of the collected light.

Figure 11A:
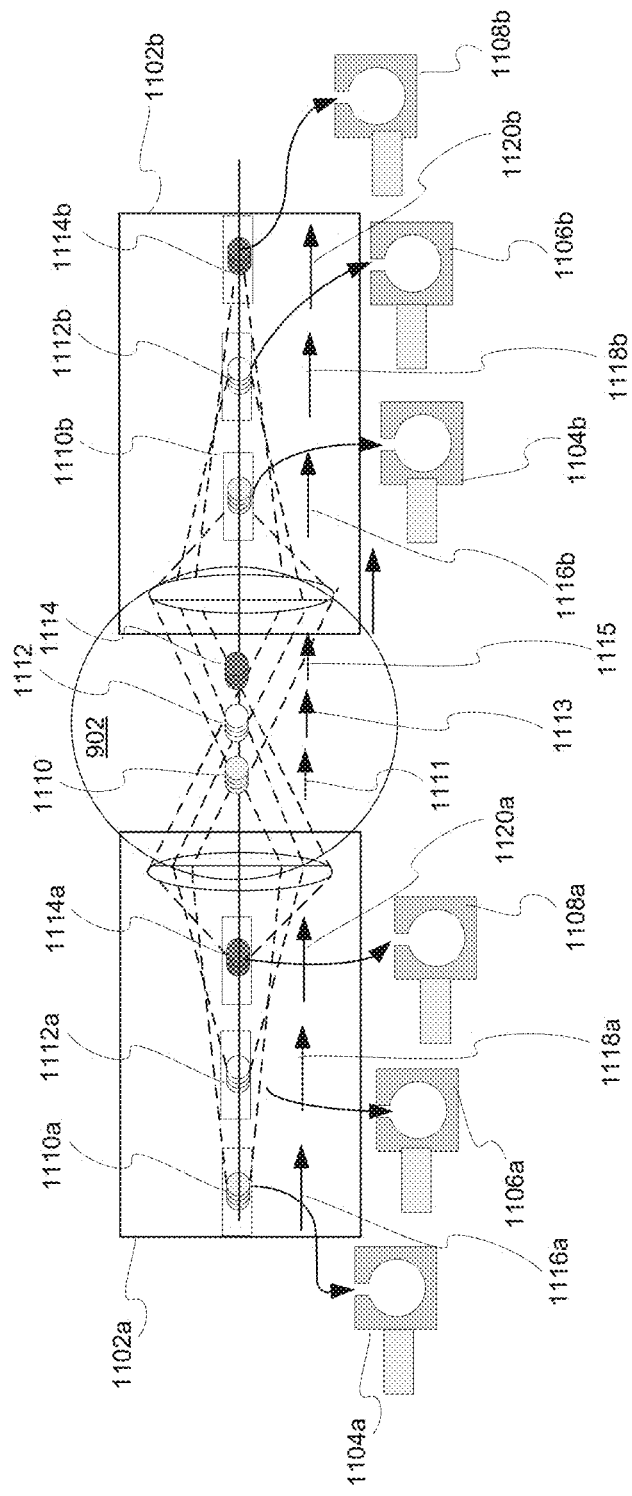
FIG. 11A is a top view representation of segmented longitudinal imaging collection system in accordance with one embodiment of the present invention.

FIG. 11A is a top view representation of the segmented longitudinal imaging aspect of one embodiment of the present invention. As shown, multiple spots 1110, 1112, and 1114 are scanned across the sample 902 along scan lines 1111, 1113, and 1115, respectively. A first side channel 1102a receives and separates longitudinal imaged scan spots 1110a, 1112a, and 1114a in corresponding scan directions 1116a, 1118a, and 1120a, respectively. Likewise, a second side channel 1102b receives and separates longitudinal imaged scan spots 1110b, 1112b, and 1114b in corresponding scan directions 1116b, 1118b, and 1120b, respectively. These imaged scan spots are sensed by corresponding sensors. Image scan spots 1110a, 1112a, and 1114a are sensed by, for example, sensor modules 1104a, 1106a, and 1108a, respectively. Likewise, image scan spots 1110b, 1112b, and 1114b are sensed by, for example, sensor modules 1104b, 1106b, and 1108b, respectively.

Figure 11B:
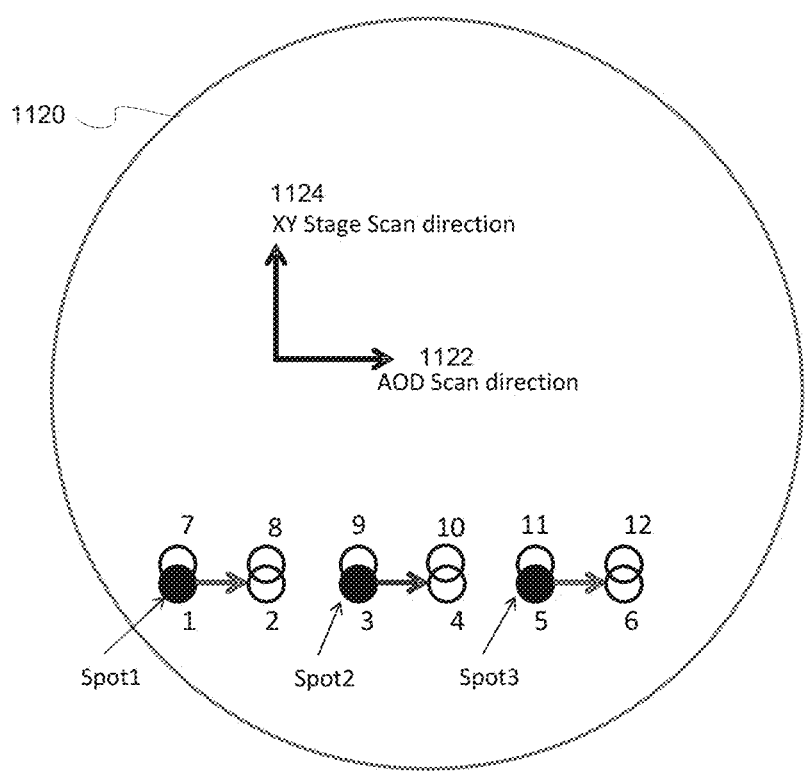
FIG. 11B illustrates one example of the scanning direction of the stage and AOD with respect to three spots.

The grazing angle of each beam may produce an elliptical spot on the wafer surface, having a major axis perpendicular to the scan line. The AOD causes each spot to scan across a short scan line equal in length to the length of scan line to produce reflected and scattered light. FIG. 11B illustrates one example of the scanning direction of the stage and AOD with respect to three spots. It is noted that the size of the spots and scans are exaggerated with respect to the wafer 1120 to better illustrate this embodiment. In this example, the AOD produces a single scanning spot, and a 3×1 DOE generates 3 spots: Spot1, Spot2, and Spot 3. The propagation of the chirp packet through the chirp AOD causes all 3 spots to scan simultaneously across wafer 1120 in AOD scan direction 1122. Spot1 scans from wafer position 1 to 2; Spot2 scans from wafer position 3 to 4; and Spot3 scans from wafer position 5 to 6. While the AOD scans each spot, the xy stage is moving in an XY stage scan direction 1124 so that the next sweep of the AOD begins with wafer positions 7, 9, and 11 and completes at positions 8, 10, and 12.

Figure 11C:
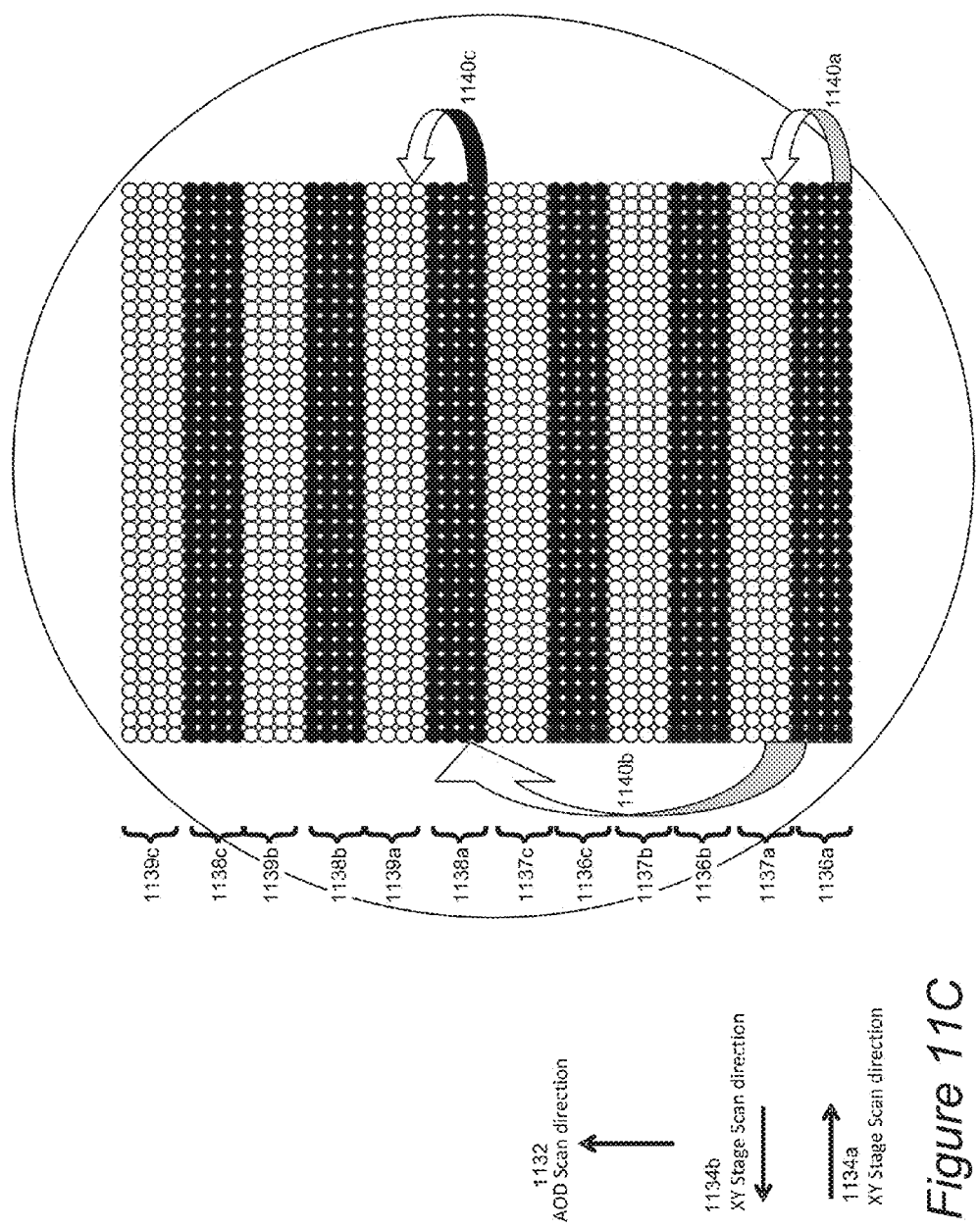
FIG. 11C is a diagrammatic representation of interleaved scanning with XY stage motion in accordance with one embodiment of the present invention.

FIG. 11C is a diagrammatic representation of interleaved scanning with XY stage motion in accordance with one embodiment of the present invention. It is noted that the size of the spots and scans are exaggerated with respect to the wafer to better illustrate this embodiment. In this example, three spots are scanned in AOD scan direction 1132 from the bottom to top of three initial ribbons 1136*a*, 1136*b*, and 1136*c*. Upon reaching the border of the first scan portions (bottom to top of each ribbon), the AOD resets and positions the spot for the next raster scan from left to right. The continuous motion of the XY stage in a direction perpendicular to the scanning spot direction now positions the beam to a new area to be inspected. For instance, the stage also moves so that the three spots are simultaneously scanned in XY stage scan direction 1134*a* (left to right) along ribbons 1136*a*, 1136*b*, and 1136*c*, respectively. After the first three ribbons 1136*a*~1136*c* are scanned, the stage steps in direction 1140*a* to move to a second set of ribbons 1137*a*, 1137*b*, and 1137*c* that will be interleaved between the first set of ribbons 1136*a*~1136*c*. After this second set of ribbons are completed (e.g., scanned in direction 1134*b*), the stage can then step in direction 1140*b* to scan a third set of ribbons 1138*a*, 1138*b*, and 1138*c* with the three spots. After this third set of ribbons 1138*a*~1138*c* are scanned, the stage can then step in direction 1140*c* to the last set of ribbons 1139*a*, 1139*b*, and 1139*c*.

Figure 11D:
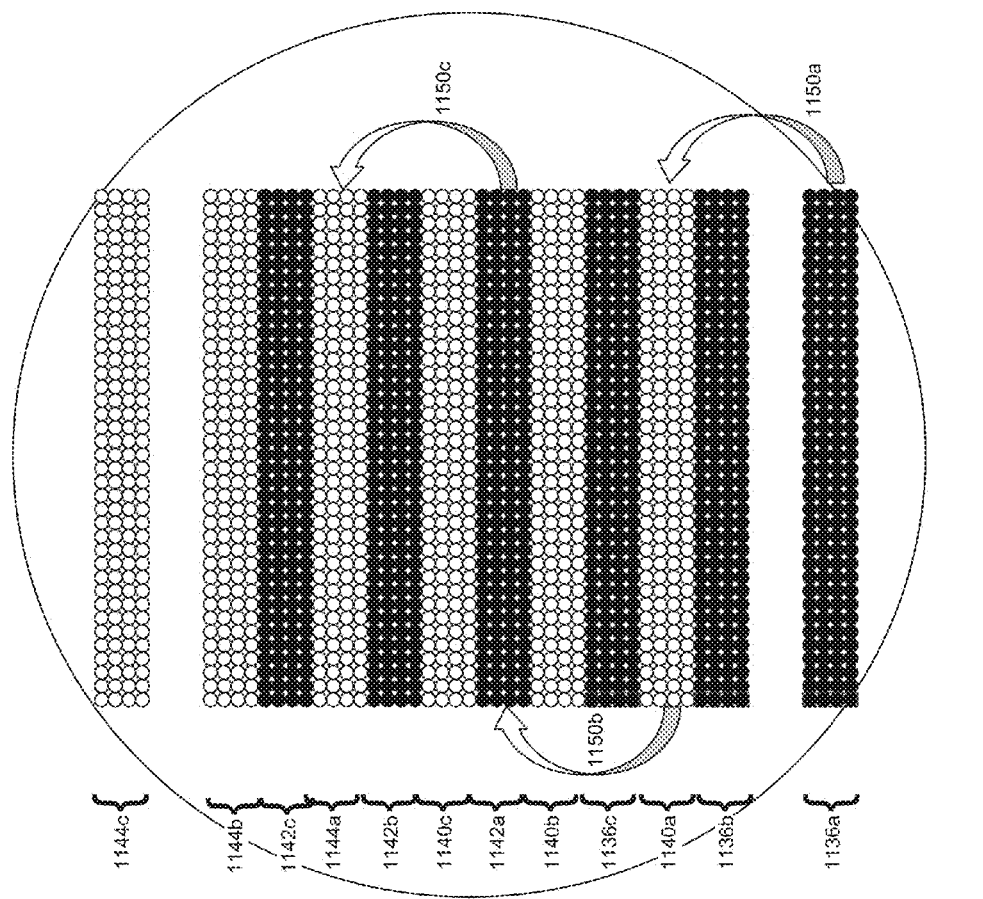
FIG. 11D is a diagrammatic representation of interleaved scanning with XY stage motion in accordance with an alternative embodiment of the present invention.

FIG. 11D is a diagrammatic representation of interleaved scanning with XY stage motion in accordance with an alternative embodiment of the present invention. In this example, the first set of ribbons 1136*a*~1136*c* are still initially scanned. However, the stage steps in direction 1150*a* for a greater distance to scan second ribbons 1140*a*, 1140*b*, and 1140*c*. The stage then steps in direction 1150*b* to scan a third set of ribbons 1142*a*, 1142*b*, and 1142*c*. Finally, the stage steps in direction 1150*c* to scan a fourth set of ribbons 1144*a*, 1144*b*, and 1144*c*. The topmost ribbon (1144*c*) and bottommost ribbon (1136*a*) may be thrown out of the analysis.

Longitudinal imaging of multiple scanned spots along the optical axis can result in minimization of certain optical aberrations. For instance, optical aberrations that require a lateral field (e.g., coma) will be minimized when imaging along the optical axis. The longitudinal imaging (with no lateral field) combined with interleaved scanning (with reduced imaging requirements) provides a simple and inexpensive way to support both a large collection angle (NA>0.9) and large FOV (FOV>1 mm). More specifically, certain system embodiments provide multiple collection channels (two longitudinal and normal) that simultaneously collect from multiple segmented scan lines.

A large FOV combined with a large collection NA may result in a high throughput, high performance system. A large FOV allows the ability to reach high throughputs. Precision XY stages are limited in terms of how fast they can move the sample under inspection. A large FOV system inspects large portions of the wafer with a minimum of XY stage operation. In addition, a large FOV and, hence, high throughput system enables the user to run higher resolution modes at the same speed.

Certain collection channel embodiments collect over a large solid angle and may be associated with increased sensitivity. A large collection solid angle ensures that the system collects the signal of interest. A large solid angle of collection also enables the suppression of noise (roughness and other sources). Additionally, the large solid angle enables the system to utilize features such as flexible aperture configurations to select regions with high signal and low noise.

Large solid angle of collection and large FOV are a result of the segmentation of the system into multiple optical channels, including longitudinal channels. Additionally, the spot isolation mechanisms described herein reduce crosstalk between spots, which would otherwise contribute to noise and false defect detection.

Figure 12:
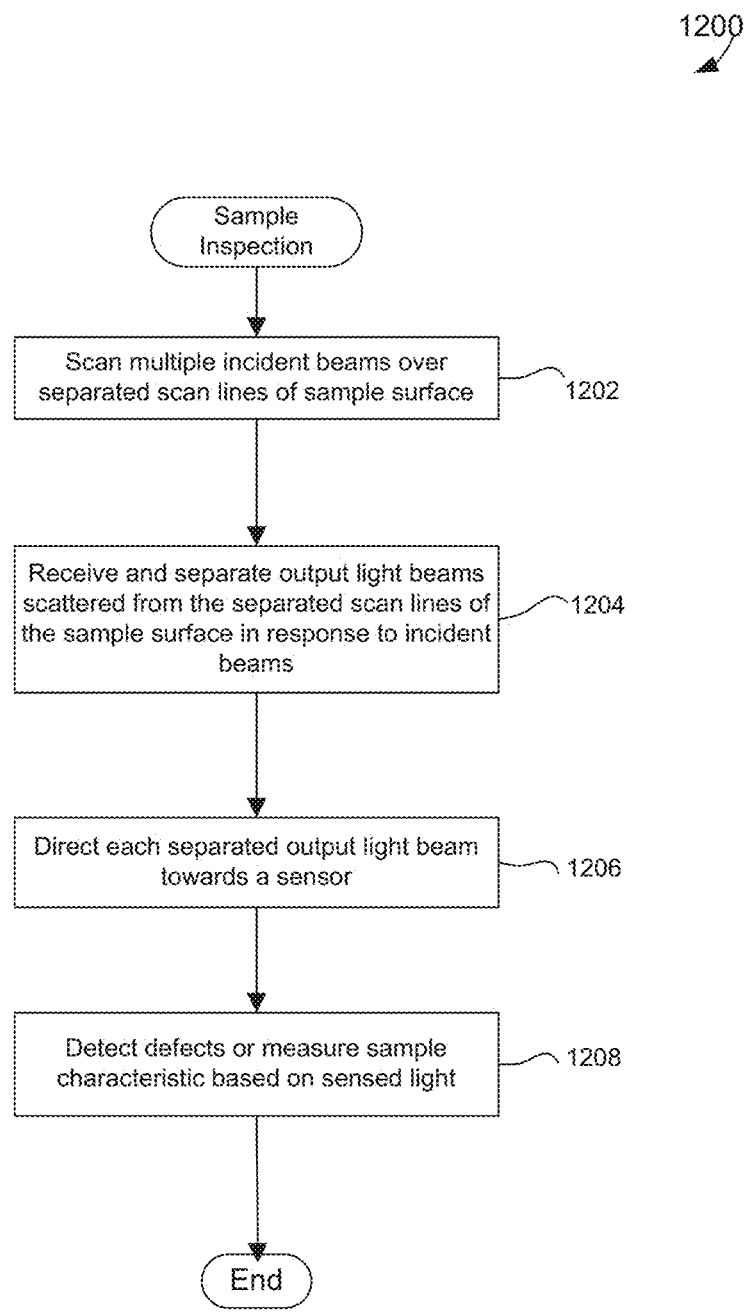
FIG. 12 is a flow chart illustrating a general procedure for inspecting a sample using a longitudinal system in accordance with one embodiment of the present invention.

FIG. 12 is a flow chart illustrating a general procedure 1200 for inspecting a sample using a longitudinal system in accordance with one embodiment of the present invention. Initially, multiple incident beams may be scanned over separated scan line portions in operation 1202. For instance, the normal and oblique incident channels of FIGS. 9A~9E may be used to generate normal and oblique incident beams in each illumination channel.

Output light scattered from the separated scan lines on the sample surface in response to the incident beams may then be received and separated in operation 1204. For example, the side and normal collection channels may be used to receive and separate light that is reflected, diffracted, and scattered from the sample scan line portions. Each separated output light beam may then be directed to a separate sensor in operation 1206. In the embodiment of FIG. 9A~9E, each separated beam from each channel 931*a*~931*c* may be collected by such channels sensors.

Defects may then be detected or sample characteristics measured based on the sensed light in operation 1208. The detected images (or signals) may generally be analyzed to determine whether defects are present on the sample. For example, the intensity values from a target die are compared to the intensity values from a corresponding portion of a reference die (or generated from a design database), where a significant intensity difference may be defined as a defect. These inspection systems may implement any suitable inspection technology, along with the longitudinal imaging mechanisms described herein. By way of examples, brightfield and/or darkfield optical inspection mechanisms may be utilized. The mechanisms of the present invention may also be implemented within a scanning electron microscopy system.

Each detected image may also be input to a defect (e.g., image) processor (e.g., 950). Defect processor may include mechanisms for processing the received data, such as buffering, compressing, packing, filtering noise, generating images based on the input signal, analyzing images to detect defects on the sample, etc. The majority of defects may be found by detecting contrast, defined as the ratio of the intensities in the target and reference dies, rather than by threshold, which is defined as the difference between the intensities.

The longitudinal collection systems described herein may be implemented on various specially configured inspection or metrology systems, such as the one schematically illustrated in FIGS. 9A~9E. In certain embodiments, a system for inspecting or measuring a specimen includes various controller components for implementing the techniques described herein. The controller may be implemented by any suitable combination of hardware and/or software, such as a processor, memory, programmable device or field programmable gate array (FPGA), etc.

The inspection system may be associated with a computer system that is configured (e.g., with programming instructions) to provide a user interface (e.g., on a computer screen) for displaying resultant inspection characteristics. The computer system may also include one or more input devices (e.g., a keyboard, mouse, joystick) for providing user input, such as changing detection parameters. In certain embodiments, the computer system is configured to carry out inspection techniques in conjunction with other inspection components, such as controller 950, detailed herein. The computer system typically has one or more processors coupled to input/output ports, and one or more memories via appropriate buses or other communication mechanisms.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Other system embodiments may include additional oblique side channels to detect light scattered from the sample surface by a plurality of detectors, in addition to longitudinal side channels. These additional collector channels can be arranged to collect light over a fixed solid angle, dependent upon, inter alia, the elevational and azimuthal angle of the channel. Those of ordinary skill in the art will readily recognize that the number and location of the collector channels and/or their collection solid angle may be changed in various alternative embodiments without departing from the scope of the invention. Several system embodiments that include additional collection channels are further described in U.S. patent application Ser. No. 13/898,736, entitled "Image Synchronization of Scanning Wafer Inspection System", filed 21 May 2013 by Kai Cao et al., which application is incorporated herein by reference in its entirety.

A bright field reflectivity/autoposition channel can also be positioned in front of the oblique incident beam to collect specularly reflected light. The bright field signal derived from this channel carries information concerning the pattern, local variations in reflectivity and height. This channel is sensitive to detecting various defects on a surface. For example, the bright field signal is sensitive to representing film thickness variations, discoloration, stains and local changes in dielectric constant. The bright field signal could be used to produce an error height signal, corresponding to a variation in wafer height, which is fed to a z-stage to adjust the height accordingly. A separate autofocus can also be inserted into the system to image through the normal collection channel. Finally, the bright field signal can be used to construct a reflectivity map of the surface. In one embodiment, this channel is basically an unfolded Type I confocal microscope operating in reflection mode. It is considered unfolded because the illuminating beam and reflected beams, here, are not collinear, as compared with a typical reflection confocal microscope in which the illuminating and reflected beams are collinear.

The brightness of a scan line produced by a system as described above may be calibrated by scanning a specimen of uniform reflectivity. Light scattered from different positions along the final scan line may be collected and measured. The amplitude of the drive signal applied to the prescan AOD may then be modulated as needed to produce a scan line of measured uniform brightness at the specimen. This calibration may compensate not only for attenuation in the chirp AOD, but for any other non-uniformities in the scanning system.

The illumination system may also include additional optical components (not shown). For example, additional optical components may include, but may not be limited to, beam splitters, quarter wave plates, polarizers such as linear and circular polarizers, rotating polarizers, rotating analyzers, collimators, focusing lenses, mirrors, dichroic mirrors, partially transmissive mirrors, filters such as spectral or polarizing filters, spatial filters, reflectors, and modulators. Each of these additional optical components may be disposed within the system or may be coupled to any of the components of the system as described herein.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the collection channels can be configured to simultaneously collect from the normal incidence and oblique incidence illumination channels. Additionally, the system may exclude a magnifier changer. Accordingly, the present embodiments are to be considered as illustrative and not restrictive, and the invention is not to be limited to the details given herein.

What is claimed is:

1. system for inspecting or measuring a specimen, comprising:
    an illumination channel for generating and scanning a plurality of incident beams to form a plurality of spots that scan across a segmented line comprised of a plurality of scan portions of the specimen; and
    one or more detection channels for sensing light emanating from a specimen in response to the incident beams directed towards such specimen and collecting a detected image for each scan portion as each incident beam's spot is scanned over its scan portion, wherein the one or more detection channels include at least one longitudinal side channel for longitudinally collecting a detected image for each scan portion as each incident beam's spot is scanned over its scan portion, wherein the at least one longitudinal side channel is arranged to have an optical axis along which the detected image is collected and which is also parallel and coincident with a plane of the specimen or an image plane of the specimen.

2. The system of claim 1, wherein the one or more detection channels include a first longitudinal side channel for longitudinally collecting a first plurality of detected images for the scan portions, a second longitudinal side channel for longitudinally collecting a second plurality of detected images for the scan portions, and a normal channel for collecting a third plurality of detected images for the scan portions, wherein the first longitudinal side channel is positioned opposite of the second longitudinal side channel.

3. The system of claim 2, wherein the illumination channel includes a normal illumination sub-channel for generating and scanning a first set of the plurality of incident beams to contribute to the plurality of spots that scan across the plurality of scan portions of the specimen and an oblique illumination sub-channel for generating and scanning a second set of the plurality of incident beams to contribute to the plurality of spots that scan across the plurality of scan portions of the specimen.

4. A system for inspecting or measuring a specimen, comprising:
an illumination channel for generating and scanning a plurality of incident beams to form a plurality of spots that scan across a segmented line comprised of a plurality of scan portions of the specimen; and
one or more detection channels for sensing light emanating from a specimen in response to the incident beams directed towards such specimen and collecting a detected image for each scan portion as each incident beam's spot is scanned over its scan portion, wherein the one or more detection channels include at least one longitudinal side channel for longitudinally collecting a detected image for each scan portion as each incident beam's spot is scanned over its scan portion, wherein:
the one or more detection channels include a first longitudinal side channel for longitudinally collecting a first plurality of detected images for the scan portions. a second longitudinal side channel for longitudinally collecting a second plurality detected images for the scan portions, and a normal channel for collecting a third plurality of detected images for the scan portions, wherein the first longitudinal side channel is positioned opposite of the second longitudinal side channel,
the illumination channel includes a normal illumination sub-channel for generating and scanning a first set of the plurality of incident beams to contribute to the plurality of spots that scan across the plurality of scan portions of the specimen and an oblique illumination sub-channel for generating and scanning a second set of the plurality of incident beams to contribute to the plurality of spots that scan across the plurality of scan portions of the specimen, and
the first longitudinal side channel comprises:
a first front lens arranged for receiving first output beams that are scattered from the scan portions and directing such first output beams through a Fourier plane towards a first back lens,
the first back lens arranged for receiving and directing the first output beams towards a first sensor module, and
the first sensor module arranged for separately sensing the first output beams from the first back lens,
the second longitudinal side channel comprises:
a second front lens arranged for receiving second output beams that are scattered from the scan portions and directing such second output beams through a Fourier plane towards a second back lens,
the second back lens arranged for receiving and directing the second output beams towards a second sensor module, and
the second sensor module arranged for separately sensing the second output beams from the second back lens; and
the normal channel comprises:
output optics for collecting and directing the third set of output beams towards a third sensor module; and
the third sensor module arranged for separately sensing the third output beams.
5. The system of claim 4, wherein:
the first longitudinal side channel further comprises:
a first optics element arranged for receiving the first output beams from the first front lens, spatially filtering portions of the first output beams at the Fourier plane, and directing the first output beams to the first back lens,
the second longitudinal side channel further comprises:
a second optics element arranged for receiving the second output beams from the second front lens, spatially filtering portions of the second output beams at the Fourier plane, and directing the second output beams to second back lens, and the normal channel further comprises:
a third optics element arranged for receiving and spatially filtering portions of the third output beams at the Fourier plane, and directing the third output beams to third sensor module.
6. The system of claim 5, wherein the first and second optics elements each include an aperture having serrated teeth pointed perpendicular to an optical axis for controlling diffraction.
7. The system of claim 6, wherein the serrated teeth are formed from two overlaid masks with serrated teeth so as to cover rounded portions of the teeth in each mask and to form non-rounded serrated teeth.
8. The system of claim 6, wherein the first and second optics elements each include a plurality of pins that are independently movable to drop down into each aperture and selectively block noise, isolate signals, or block one or more diffraction spots.
9. The system of claim 4, wherein the normal and oblique illumination sub-channels each comprise a magnifier changer.
10. The system of claim 9, wherein:
the normal, first and second longitudinal side channels exclude a magnifier changer so as to have a fixed magnification for the first, second, and third output beams,
the normal and oblique illumination sub-channels each include a diffractive optical element (DOE) positioned after such sub-channel's magnifier changer, wherein the DOE's of the normal and oblique illumination sub-channels are arranged to generate the first and second set of incident beams, respectively, so that the first and second set of incident beams have a same center scan position at different magnifications; and
the first, second, and third sensor modules include a first, second, and third spot separator mechanism, respectively, that are sized and positioned to separately receive the first, second, third output beams, respectively, at a highest and lowest magnification without movement of such spot separator mechanism.
11. The system of claim 10, wherein the normal and oblique illumination sub-channels each include a scan mechanism that is configured to sweep the first and second set of output beams across equally sized scan portions on the sample.
12. The system of claim 9, wherein the normal channel and the first and second longitudinal side channels each include a magnifier changer to match a magnification of the magnifier changer of the normal and oblique illumination sub-channels.
13. The system of claim 4, wherein
the first sensor module comprises:
a first and second razor portion forming a first gap therebetween arranged to receive a focus point for each of the first output beams,
a first plurality of prisms that are each positioned at each of the first output beams' focus point so as to separately receive and direct the first output beams to a plurality of first fiber elements, the first fiber elements arranged to separately receive and direct the first output beams from the first plurality of prisms to a first plurality of focusing elements, the first plurality of focusing elements being arranged for individually focusing the first output beams onto a plurality of first sensor elements, and the first plurality of sensor elements being positioned for individually sensing the first output beams, the second sensor module comprises:

a third and fourth razor portion forming a second gap there between arranged to receive a focus point for each of the second output beams, a second plurality of prisms that are each positioned at each of the second output beams' focus point so as to separately receive and direct the second output beams to a plurality of second fiber elements, the second fiber elements arranged to separately receive and direct the second output beams from the second plurality of prisms to a second plurality of focusing elements, the second plurality of focusing elements being arranged for individually focusing the second output beams onto a plurality of second sensor elements, and the second plurality of sensor elements being positioned for individually sensing the second output beams, and the third sensor module comprises:

a fifth and sixth razor portion forming a third gap there between arranged to receive a focus point for each of the third output beams, a third plurality of prisms that are each positioned at each of the third output beams' focus point so as to separately receive and direct the third output beams to a plurality of third fiber elements, the third fiber elements arranged to separately receive and direct the third output beams from the third plurality of prisms to a third plurality of focusing elements, the third plurality of focusing elements being arranged for individually focusing the third output beams onto a plurality of second sensor elements, and the third plurality of sensor elements being positioned for individually sensing the third output beams.

14. The system of claim 13, wherein the first, second, and third prisms are movable to compensate for distortion.

15. The system of claim 4, wherein:

the first sensor module comprises:

a first and second razor portion forming a first gap there between arranged to receive a focus point for each of the first output beams, a first plurality of mirror and/or fiber elements sets that are each positioned at each of the first output beams' focus point no as to separately receive and direct the first output beams to a first plurality of focusing elements, the first plurality of focusing elements being arranged for individually focusing first output beams onto a plurality of first sensor elements, and the first plurality of sensor elements being positioned for individually sensing the first output beams, the second sensor module comprises:

a third and fourth razor portion forming a second gap there between arranged to receive a focus point for each of the second output beams, a second plurality of mirror and/or fiber elements sets that are each positioned at each of the second output beams' focus point so as to separately receive and direct the second output beams to a second plurality of focusing elements, the second plurality of focusing elements being arranged for individually focusing the second output beams onto a plurality of second sensor elements, and the second plurality of sensor elements being positioned for individually sensing the second output beams, and the third sensor module comprises:

a fourth and fifth razor portion forming a third gap there between arranged to receive a focus point for each of the third output beams, a third plurality of mirror and/or fiber elements sets that are each positioned at each of the third output beams' focus point so as to separately receive and direct the third output beams to a third plurality of focusing elements, the third plurality of focusing elements being arranged for individually focusing the third output beams onto a plurality of third sensor elements, and the third plurality of sensor elements being positioned for individually sensing the third output beams.

16. The system of claim 4, wherein:

the first sensor module comprises:

a first mask having a plurality of apertures that each receive a focus point for each of the first output beams, a first plurality of prisms or sets of mirrors that are each positioned at each of the first output beams' focus point so as to separately receive and direct the first output beams to a plurality of first fiber elements, the first fiber elements arranged to separately receive and direct the first output beams from the first plurality of prisms to a first plurality of focusing elements, the first plurality of focusing elements being arranged for individually focusing the first output beams onto a plurality of first sensor elements, and the first plurality of sensor elements being positioned for individually sensing the first output beams, the second sensor module comprises:

a second mask having a plurality of apertures that each receive a focus point for each of the second output beams, a second plurality of prisms or sets of mirrors that are each positioned at each of the second output beams' focus point so as to separately receive and direct the second output beams to a plurality of second fiber elements, the second fiber elements arranged to separately receive and direct the second output beams from the second plurality of prisms to a second plurality of focusing elements, the second plurality of focusing elements being arranged for individually focusing the second output beams onto a plurality of second sensor elements, and the second plurality of sensor elements being positioned for individually sensing the second output beams, and the third sensor module comprises:
- a third mask having a plurality of apertures that each receive a focus point for each of the third output beams,
- a third plurality of prisms or sets of mirrors that are each positioned at each of the third output beams' focus point so as to separately receive and direct the third output beams to a plurality of third fiber elements,
- the third fiber elements arranged to separately receive and direct the third output beams from the third plurality of prisms to a third plurality of focusing elements,
- the third plurality of focusing elements being arranged for individually focusing the third output beams onto a plurality of third sensor elements, and
- the third plurality of sensor elements being positioned for individually sensing the third output beams.

17. The system of claim 16, wherein each of the first, second, and third masks includes a grating in each aperture for directing the first, second, and third output beams, respectively towards the first, second, and third sensor elements, respectively.

18. The system of claim 17, wherein at least some of the gratings of the first, second, and third mask have orientations in different directions.

19. The system of claim 17, wherein the gratings of the first, second, and third mask have orientations in a same direction.

20. A method of inspecting a specimen, comprising:
- scanning multiple incident beams over separated scan lines of the specimen;
- receiving and separating output beams scattered from the separated scan lines of the specimen in response to the incident beams;
- longitudinally directing each separated output beam towards a sensor to longitudinally generate an image or signal, wherein each separated output beam is directed along an optical axis along which each scan line is imaged and which is also parallel and coincident with a plane of the specimen or an image plane of the specimen; and
- detecting defects or measuring a characteristic of the specimen based on e image or signal from each sensor.

* * * * *